US012673022B2

(12) United States Patent
Hotta et al.

(10) Patent No.: US 12,673,022 B2
(45) Date of Patent: Jul. 7, 2026

(54) DRUG DELIVERY SYSTEM USING SOLUTION

(71) Applicants: Kyoto University, Kyoto (JP); Takeda Pharmaceutical Company Limited, Osaka (JP)

(72) Inventors: Akitsu Hotta, Kyoto (JP); Naoko Ishihara, Kyoto (JP); Ryuichi Nishigaki, Kanagawa (JP); Masaki Seto, Kanagawa (JP)

(73) Assignees: Kyoto University, Kyoto (JP); Takeda Pharmaceutical Company Limited, Osaka (JP)

( * ) Notice: Subject to any disclaimer, the term of this patent is extended or adjusted under 35 U.S.C. 154(b) by 1066 days.

(21) Appl. No.: 17/298,460

(22) PCT Filed: Nov. 29, 2019

(86) PCT No.: PCT/JP2019/046777
§ 371 (c)(1),
(2) Date: May 28, 2021

(87) PCT Pub. No.: WO2020/111229
PCT Pub. Date: Jun. 4, 2020

(65) Prior Publication Data

US 2022/0023207 A1 Jan. 27, 2022

(30) Foreign Application Priority Data

Nov. 30, 2018 (JP) ................................ 2018-224965

(51) Int. Cl.

| | |
|---|---|
| ***A61K 9/08*** | (2006.01) |
| ***A61K 31/7088*** | (2006.01) |
| ***A61K 38/46*** | (2006.01) |
| ***A61K 47/10*** | (2017.01) |
| ***A61K 47/12*** | (2006.01) |
| ***A61K 47/16*** | (2006.01) |
| ***A61K 47/18*** | (2017.01) |
| ***A61K 47/22*** | (2006.01) |
| ***A61K 47/24*** | (2006.01) |
| ***A61K 47/26*** | (2006.01) |
| ***A61K 48/00*** | (2006.01) |

(52) U.S. Cl.
CPC ............ *A61K 9/08* (2013.01); *A61K 31/7088* (2013.01); *A61K 38/465* (2013.01); *A61K 47/10* (2013.01); *A61K 47/12* (2013.01); *A61K 47/16* (2013.01); *A61K 47/18* (2013.01); *A61K 47/183* (2013.01); *A61K 47/22* (2013.01); *A61K 47/24* (2013.01); *A61K 47/26* (2013.01); *A61K 48/00* (2013.01)

(58) Field of Classification Search
CPC .... A61K 9/08; A61K 31/7088; A61K 38/465; A61K 47/10; A61K 47/12; A61K 47/16; A61K 47/18; A61K 47/183; A61K 47/22; A61K 47/24; A61K 47/26; A61K 48/00
See application file for complete search history.

(56) References Cited

U.S. PATENT DOCUMENTS 5,460,831 A * 10/1995 Kossovsky .......... A61K 9/0019 424/490
2001/0039264 A1* 11/2001 Abe .......................... A23L 5/00 514/400

(Continued)

FOREIGN PATENT DOCUMENTS

CA 3045131 A1 6/2018
CN 102100693 A 6/2011

(Continued)

OTHER PUBLICATIONS

Ortega (Frontiers in Bioengineering and Biotechnology. 8:887. p. 1-36) (Year: 2020).*

(Continued)

*Primary Examiner* — Kortney L. Klinkel
*Assistant Examiner* — Richard Grant Peckham
(74) *Attorney, Agent, or Firm* — Foley & Lardner LLP

(57) ABSTRACT

Provided are methods for transducing a molecule(s) of interest into a cell, comprising a step of contacting the cell with the molecule(s) of interest and a solution for transduction, the solution for transduction containing: at least one of the following (A1) to (A5); and (B) a salt: (A1) a compound represented by formula (I) excluding a predetermined compound, or a salt thereof; (A2) a compound represented by formula (II), or a salt thereof; (A3) a nucleic-acid base or the like, or a salt thereof; (A4) a compound represented by formula (III), or a salt thereof, excluding malic acid; and (A5) at least one selected from the group consisting of creatinine, hydroxyproline, 1,3-butanediol, trientine, D-cellobiose, 1,3-dimethylurea, pantolactone and trimethadione, or a salt thereof.

I

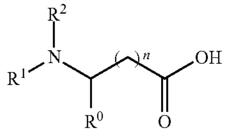

II

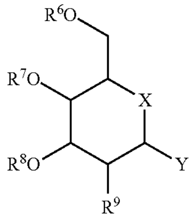

III

Rx—CRyRzCOOH

9 Claims, 8 Drawing Sheets

Specification includes a Sequence Listing.

(56) References Cited

U.S. PATENT DOCUMENTS

| | | | |
|---|---|---|---|
| 2008/0145413 A1 | 6/2008 | Panzner et al. |
| 2016/0273001 A1 | 9/2016 | Geijsen et al. |
| 2018/0221402 A1 | 8/2018 | Prieve et al. |
| 2018/0327783 A1 | 11/2018 | Geijsen et al. |

FOREIGN PATENT DOCUMENTS

| | | | | |
|---|---|---|---|---|
| CN | 103800367 A | 5/2014 | |
| CN | 107530436 A | 1/2018 | |
| JP | 09-020661 A | 1/1997 | |
| JP | 2010-513354 A | 4/2010 | |
| JP | 2015-097508 A | 5/2015 | |
| JP | 2016-535999 A | 11/2016 | |
| WO | WO-2013/049615 A1 | 4/2013 | |
| WO | WO-2015/028969 A2 | 3/2015 | |
| WO | WO-2017093326 A1 * | 6/2017 | ............ A61K 33/14 |

OTHER PUBLICATIONS

Daniel (Analytical Biochemistry 239, 130-135 (1996) Article No. 0307) (Year: 1996).*

Esbilac (PetAg Esbilac Puppy Milk . . . , Chewy.com, 2024, p. 1-9, https://www.chewy.com/petag-esbilac-powder-milk-supplement . . . ) (Year: 2024).*

Lopez (Ann Neurol 2017;81:641-652) (Year: 2017).*

Johansen (Circ Res. 2017;121:1168-1181) (Year: 2017).*

Higashino et al., "Pantothenic Acid and Metabolic Syndrome," Kagaku to Seibutsu (Science and Organism), 2008, 46(6):400-404, with partial English translation.

Office Action dated Sep. 19, 2023 in JP 2020-557853, with English translation.

D'Astolfo et al., "Efficient Intracellular Delivery of Native Proteins," Cell, Apr. 23, 2015, 161:674-690.

International Search Report dated Mar. 3, 2020 in PCT/JP2019/046777.

Staahl et al., "Efficient genome editing in the mouse brain by local delivery of engineered Cas9 ribonucleoprotein complexes," Nature Biotechnology, May 2017, 35(5):431-437.

Office Action dated Nov. 3, 2023 in TW 108143721, with English translation.

Dong et al., "Cross-linked Polyethylenimine as Potential DNA Vector for Gene Delivery with High Efficiency and Low Cytotoxicity," Acta Biochimica et Biophysica Sinica, Nov. 1, 2006, 38(11):780-787.

Sigma Aldrich, "Calcium Pantothenate," Merck, Jan. 1, 2017, 5 pages.

Supplementary European Search Report dated Aug. 22, 2022 in EP 19889710.0.

Office Action and Search Report dated Feb. 21, 2024 in CN 201980078199.0, with English translation.

Yang et al., "Advances in nucleic acid delivery vectors for gene therapy," J. Shanxi Med. Univ., Mar. 31, 2018, 49(3):300-315, with English translation.

Bayer Australia Ltd., Berocca Performance Original Berry Flavour oral solution, ARTG Entry: 232633, Jan. 13, 2015.

Kruger ANZ, Essential Health Everyday Health Vitamins B+C Effervescent Tablets—Original, ARTG Entry: 221230, Mar. 13, 2014.

Office Action dated Sep. 4, 2024 in AU 2019388011.

Office Action dated Oct. 15, 2025 in CA 3121321.

* cited by examiner

[Fig. 1]
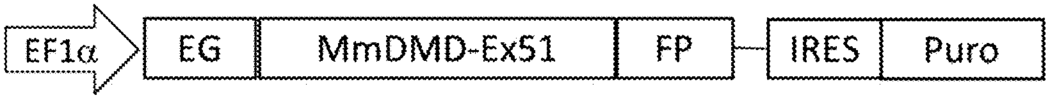
[Fig. 2]
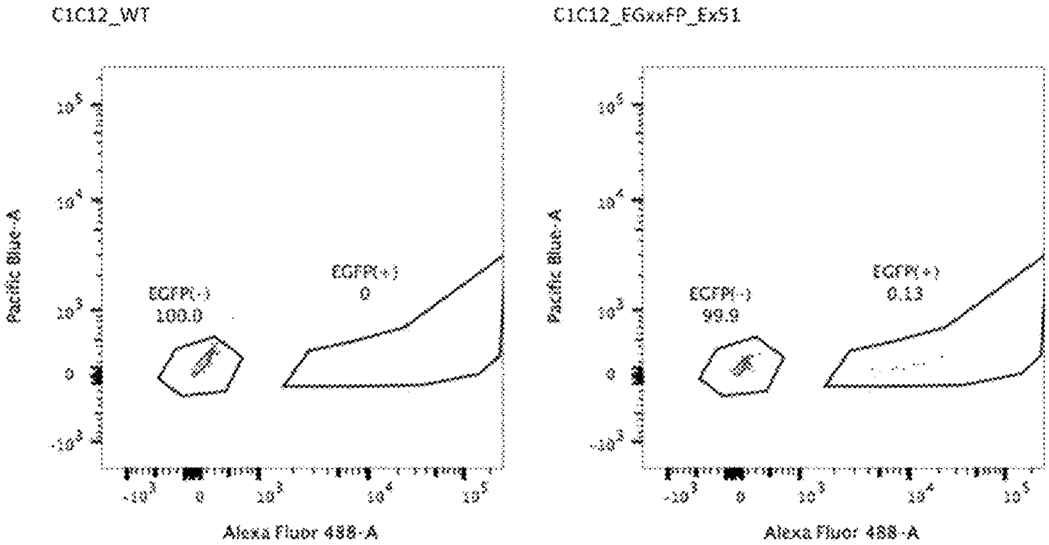
[Fig. 3]
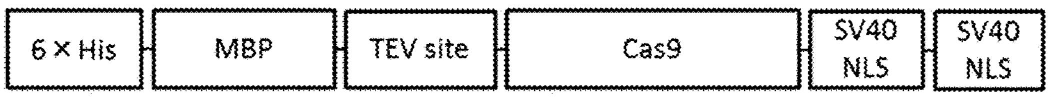

[Fig. 4-1]
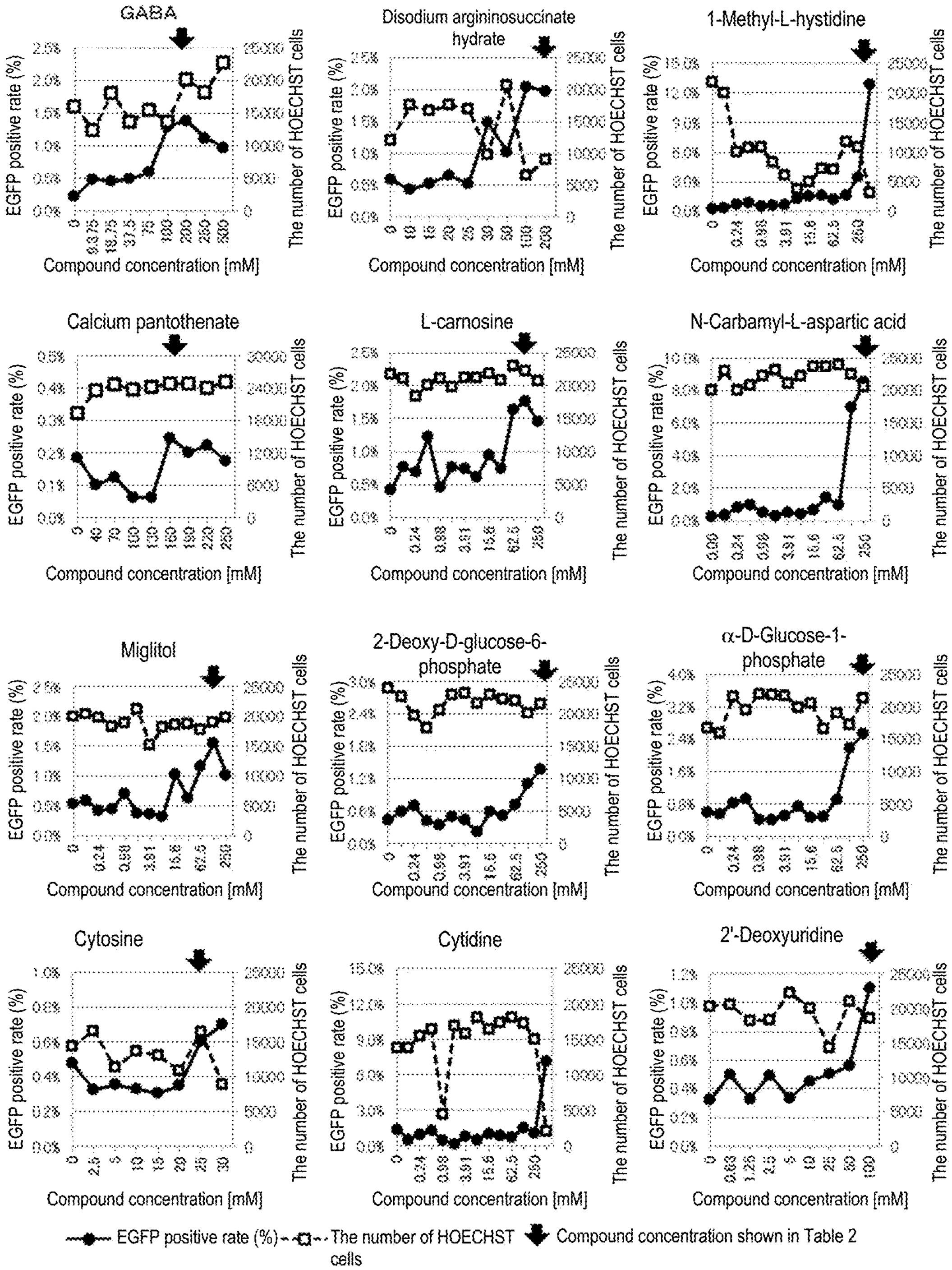

[Fig. 4-2]
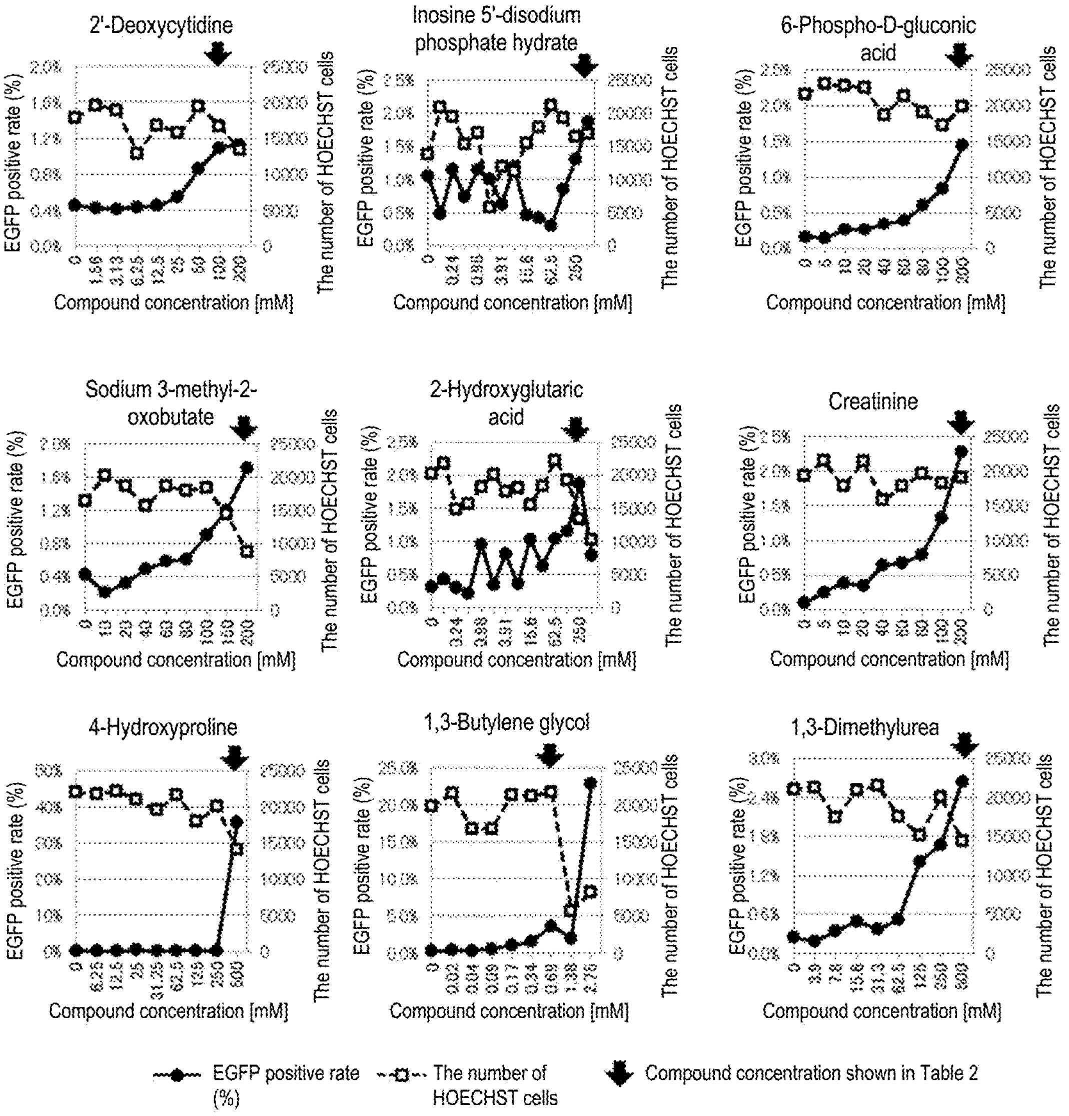

[Fig. 5]
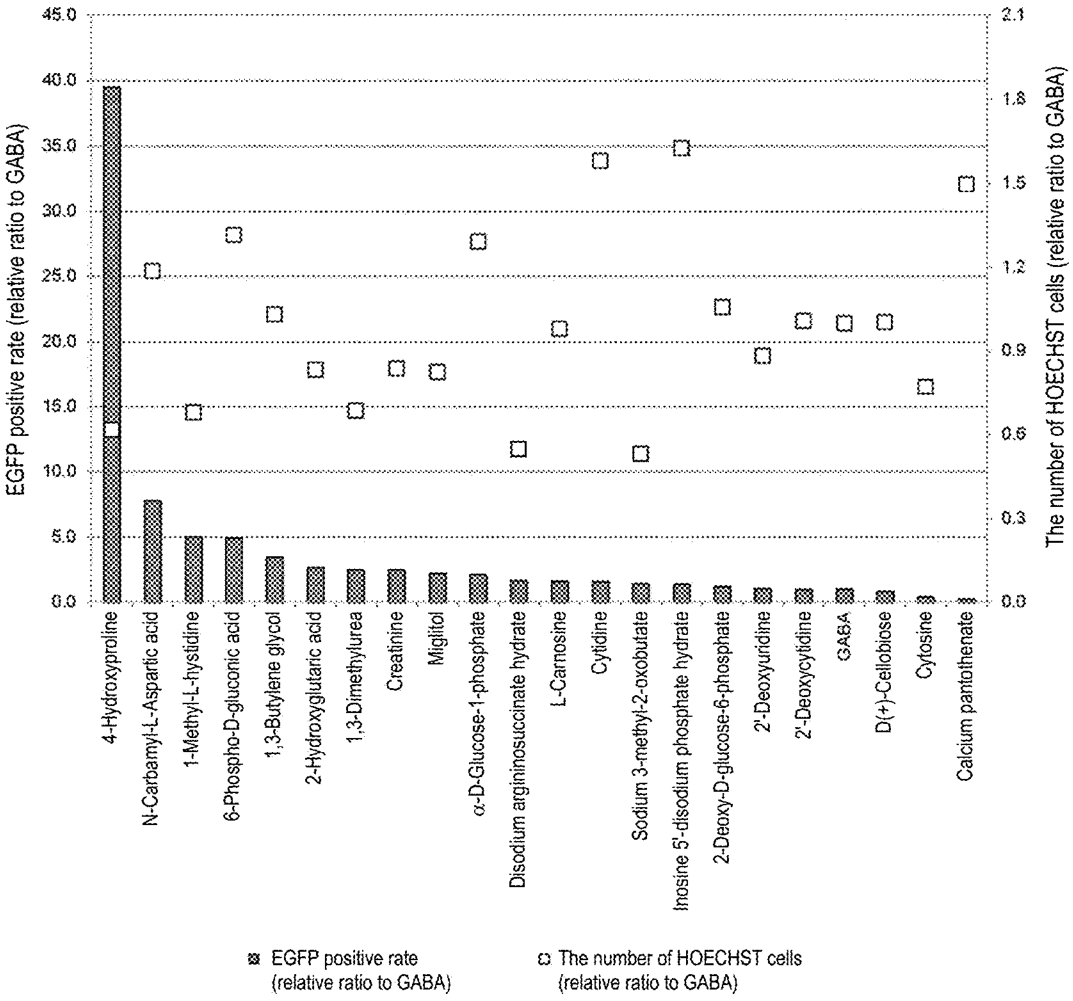

[Fig. 6]
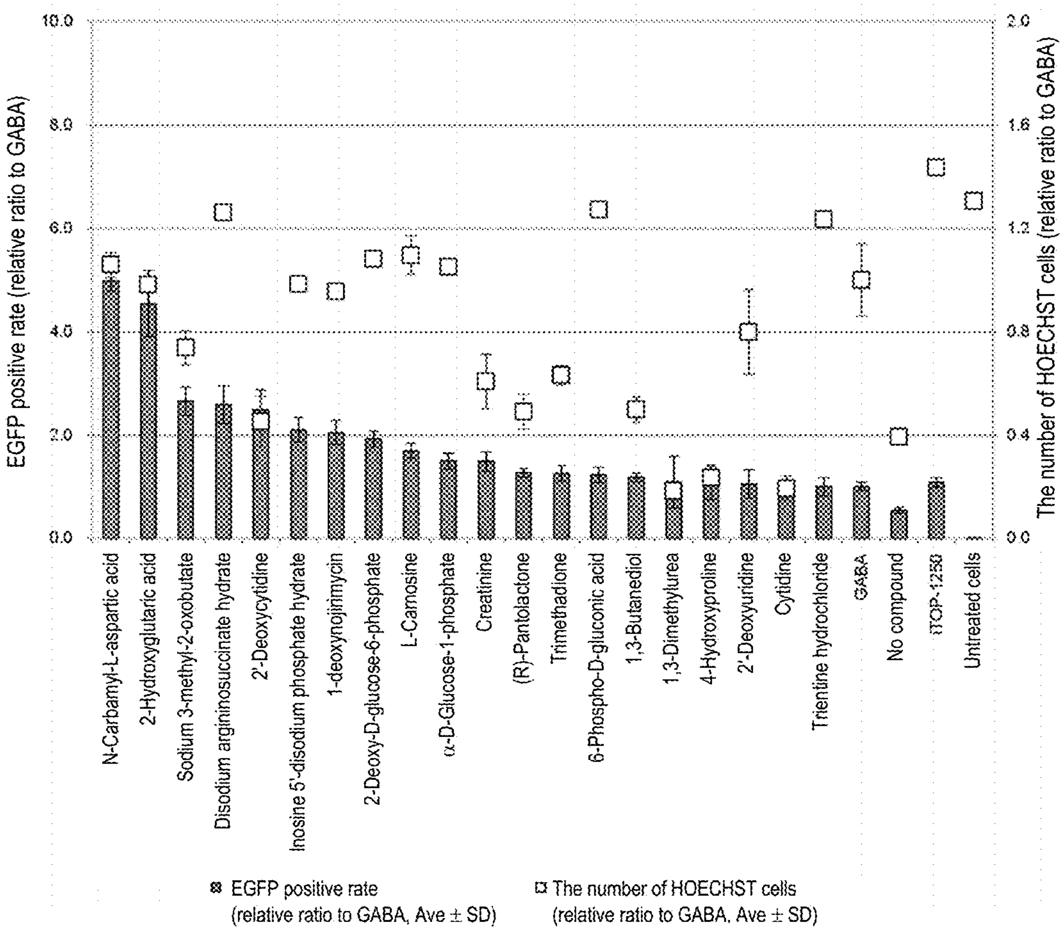

[Fig. 7]
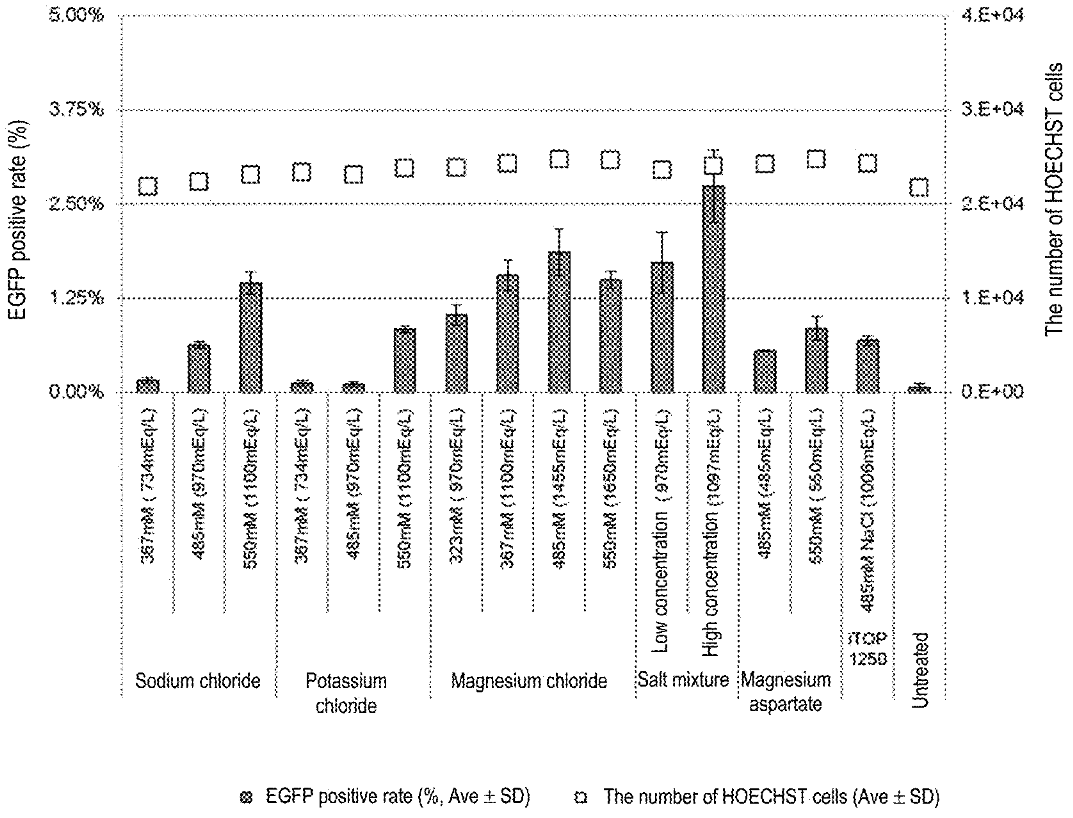
[Fig. 8]
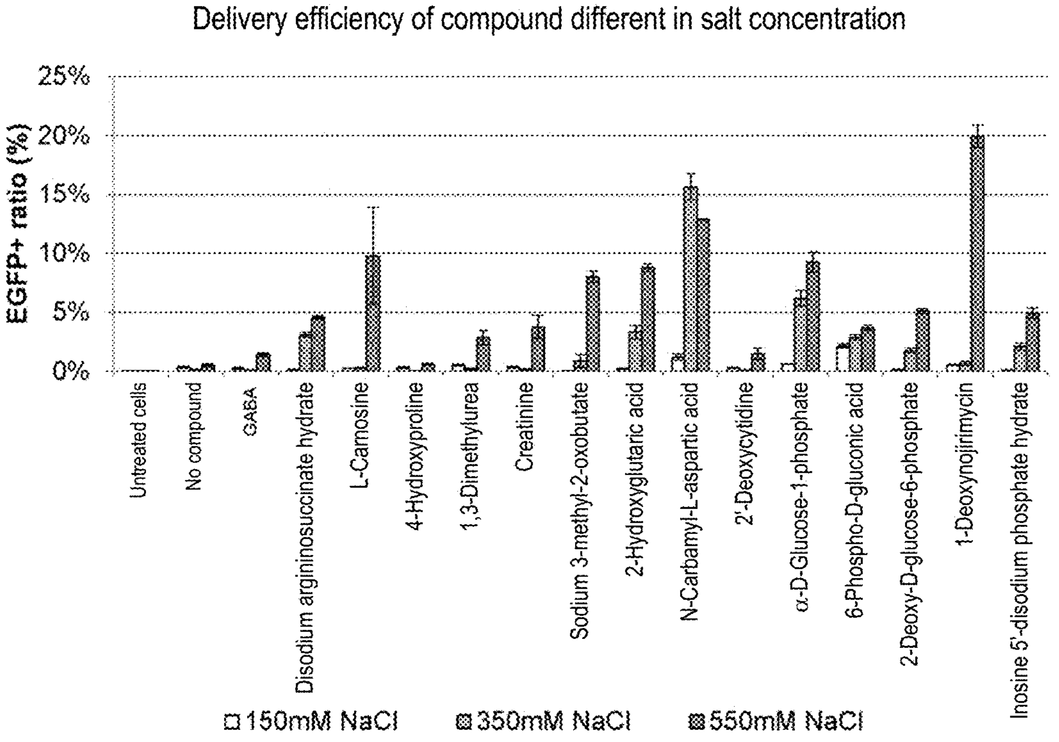

[Fig. 9]
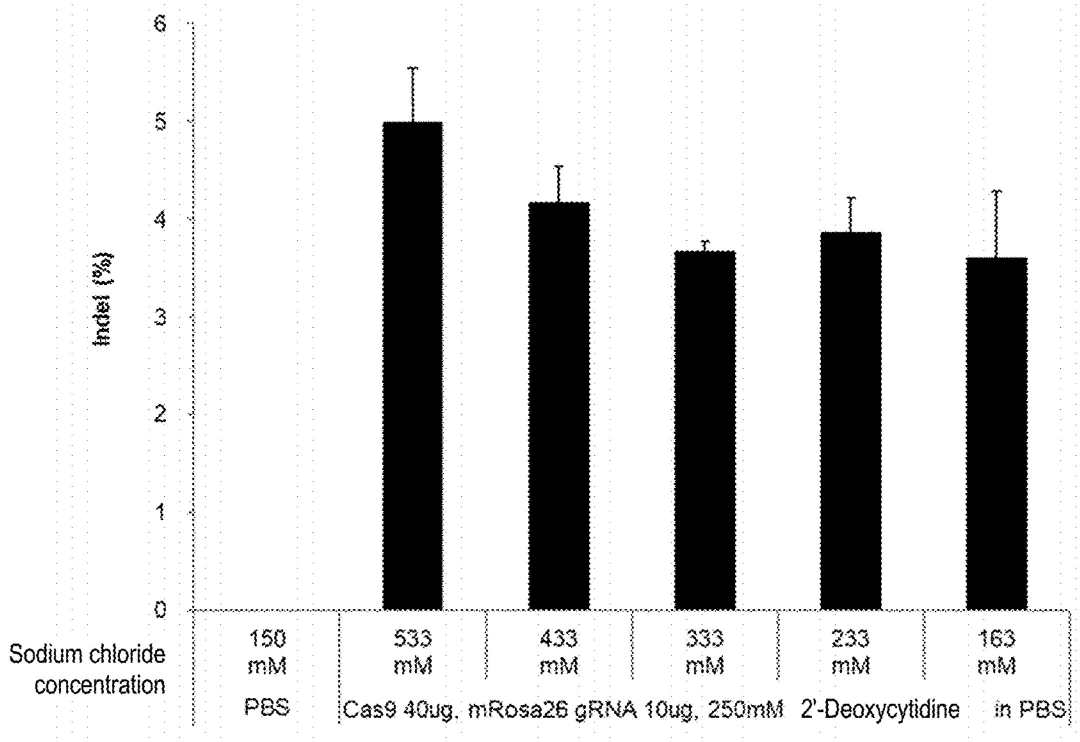
[Fig. 10]
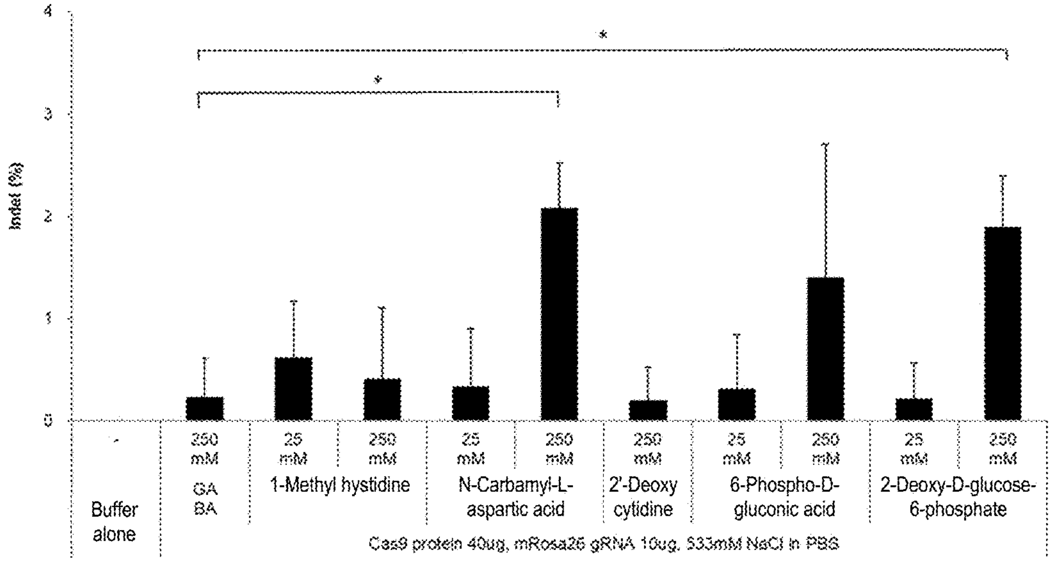
Mean ± SD, n=3. *:p<0.05 vs GABA by Dunnett test.

[Fig. 11]
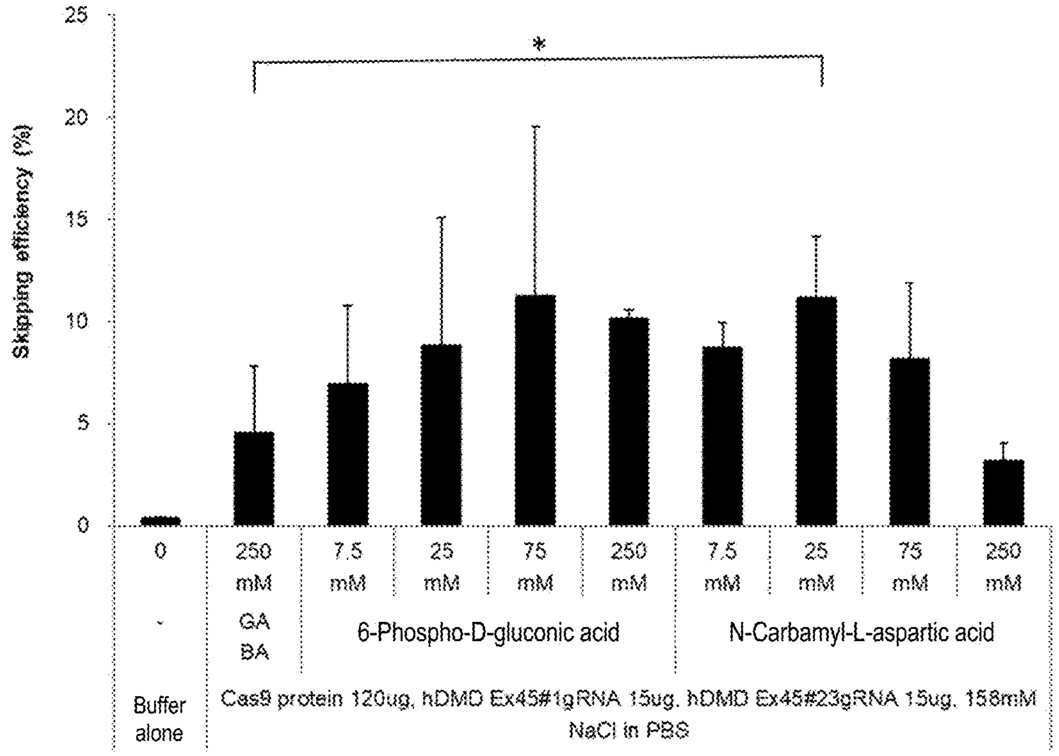
Mean ± SD, n=4. *:p<0.05 vs GABA by Dunnett test.
[Fig. 12]
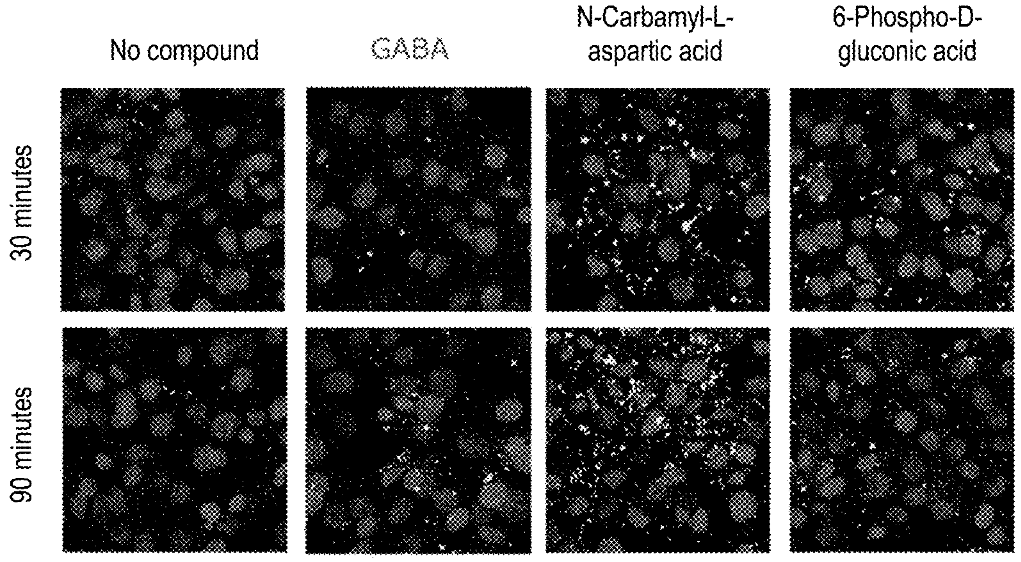

SEQUENCE LISTING

```
<160> NUMBER OF SEQ ID NOS: 19

<210> SEQ ID NO 1
<211> LENGTH: 42
<212> TYPE: RNA
<213> ORGANISM: Artificial Sequence
<220> FEATURE:
<223> OTHER INFORMATION: MmDmdEx51 crRNA
<220> FEATURE:
<221> NAME/KEY: modified_base
<222> LOCATION: (1)..(1)
<223> OTHER INFORMATION: 2'-O-methylcytidine (cm)
<220> FEATURE:
<221> NAME/KEY: modified_base
<222> LOCATION: (2)..(2)
<223> OTHER INFORMATION: 2'-O-methyladenosine
<220> FEATURE:
<221> NAME/KEY: modified_base
<222> LOCATION: (3)..(3)
<223> OTHER INFORMATION: 2'-O-methylcytidine (cm)
<220> FEATURE:
<221> NAME/KEY: modified_base
<222> LOCATION: (39)..(39)
<223> OTHER INFORMATION: 2'-O-methyluridine (um)
<220> FEATURE:
<221> NAME/KEY: modified_base
<222> LOCATION: (40)..(40)
<223> OTHER INFORMATION: 2'-O-methyluridine (um)
<220> FEATURE:
<221> NAME/KEY: modified_base
<222> LOCATION: (41)..(41)
<223> OTHER INFORMATION: 2'-O-methyluridine (um)

<400> SEQUENCE: 1

cacuagagua acagucugac guuuuagagc uaugcuguuu ug                          42


<210> SEQ ID NO 2
<211> LENGTH: 70
<212> TYPE: RNA
<213> ORGANISM: Artificial Sequence
<220> FEATURE:
<223> OTHER INFORMATION: tracrRNA
<220> FEATURE:
<221> NAME/KEY: modified_base
<222> LOCATION: (1)..(1)
<223> OTHER INFORMATION: 2'-O-methylcytidine (cm)
<220> FEATURE:
<221> NAME/KEY: modified_base
<222> LOCATION: (2)..(2)
<223> OTHER INFORMATION: 2'-O-methyladenosine
<220> FEATURE:
```

<221> NAME/KEY: modified_base
<222> LOCATION: (3)..(3)
<223> OTHER INFORMATION: 2'-O-methyladenosine
<220> FEATURE:
<221> NAME/KEY: modified_base
<222> LOCATION: (4)..(4)
<223> OTHER INFORMATION: 2'-O-methyladenosine
<220> FEATURE:
<221> NAME/KEY: modified_base
<222> LOCATION: (67)..(67)
<223> OTHER INFORMATION: 2'-O-methylguanosine (gm)
<220> FEATURE:
<221> NAME/KEY: modified_base
<222> LOCATION: (68)..(68)
<223> OTHER INFORMATION: 2'-O-methyluridine (um)
<220> FEATURE:
<221> NAME/KEY: modified_base
<222> LOCATION: (69)..(69)
<223> OTHER INFORMATION: 2'-O-methylguanosine (gm)
<220> FEATURE:
<221> NAME/KEY: modified_base
<222> LOCATION: (70)..(70)
<223> OTHER INFORMATION: 2'-O-methylcytidine (cm)

<400> SEQUENCE: 2
caaaacagca uagcaaguua aaauaaggcu aguccguuau caacuugaaa aaguggcacc 60
gagucggugc 70

<210> SEQ ID NO 3
<211> LENGTH: 101
<212> TYPE: RNA
<213> ORGANISM: Artificial Sequence
<220> FEATURE:
<223> OTHER INFORMATION: MmDmd Ex51 gRNA#1
<220> FEATURE:
<221> NAME/KEY: modified_base
<222> LOCATION: (1)..(1)
<223> OTHER INFORMATION: 2'-O-methyluridine (um)
<220> FEATURE:
<221> NAME/KEY: modified_base
<222> LOCATION: (2)..(2)
<223> OTHER INFORMATION: 2'-O-methylcytidine (cm)
<220> FEATURE:
<221> NAME/KEY: modified_base
<222> LOCATION: (3)..(3)
<223> OTHER INFORMATION: 2'-O-methyladenosine
<220> FEATURE:
<221> NAME/KEY: modified_base
<222> LOCATION: (98)..(98)
<223> OTHER INFORMATION: 2'-O-methyladenosine
<220> FEATURE:
<221> NAME/KEY: modified_base
<222> LOCATION: (99)..(99)
<223> OTHER INFORMATION: 2'-O-methyladenosine
<220> FEATURE:
<221> NAME/KEY: modified_base
<222> LOCATION: (100)..(100)
<223> OTHER INFORMATION: 2'-O-methyladenosine

<400> SEQUENCE: 3
ucacuagagu aacagucuga cguuuuagag cuagaaauag caaguuaaaa uaaggcuagu 60
ccguuaucaa cuugaaaaag uggcaccgag ucggugcuuu u 101

<210> SEQ ID NO 4
<211> LENGTH: 94
<212> TYPE: RNA
<213> ORGANISM: Artificial Sequence
<220> FEATURE:
<223> OTHER INFORMATION: mRosa26 gRNA
<220> FEATURE:
<221> NAME/KEY: modified_base
<222> LOCATION: (1)..(1)
<223> OTHER INFORMATION: 2'-O-methylguanosine (gm)

<220> FEATURE:
<221> NAME/KEY: modified_base
<222> LOCATION: (2)..(2)
<223> OTHER INFORMATION: 2'-O-methyladenosine
<220> FEATURE:
<221> NAME/KEY: modified_base
<222> LOCATION: (3)..(3)
<223> OTHER INFORMATION: 2'-O-methyluridine (um)
<220> FEATURE:
<221> NAME/KEY: modified_base
<222> LOCATION: (91)..(91)
<223> OTHER INFORMATION: 2'-O-methylguanosine (gm)
<220> FEATURE:
<221> NAME/KEY: modified_base
<222> LOCATION: (92)..(92)
<223> OTHER INFORMATION: 2'-O-methyluridine (um)
<220> FEATURE:
<221> NAME/KEY: modified_base
<222> LOCATION: (93)..(93)
<223> OTHER INFORMATION: 2'-O-methylguanosine (gm)

<400> SEQUENCE: 4
gaugggcggg agucuucugu uuuagagcua gaaauagcaa guuaaaauaa ggcuaguccg 60
uuaucaacuu gaaaaagugg caccgagucg gugc 94

<210> SEQ ID NO 5
<211> LENGTH: 96
<212> TYPE: RNA
<213> ORGANISM: Artificial Sequence
<220> FEATURE:
<223> OTHER INFORMATION: hEx45#1 gRNA
<220> FEATURE:
<221> NAME/KEY: modified_base
<222> LOCATION: (1)..(1)
<223> OTHER INFORMATION: 2'-O-methyluridine (um)
<220> FEATURE:
<221> NAME/KEY: modified_base
<222> LOCATION: (2)..(2)
<223> OTHER INFORMATION: 2'-O-methylguanosine (gm)
<220> FEATURE:
<221> NAME/KEY: modified_base
<222> LOCATION: (3)..(3)
<223> OTHER INFORMATION: 2'-O-methylguanosine (gm)
<220> FEATURE:
<221> NAME/KEY: modified_base
<222> LOCATION: (93)..(93)
<223> OTHER INFORMATION: 2'-O-methylguanosine (gm)
<220> FEATURE:
<221> NAME/KEY: modified_base
<222> LOCATION: (94)..(94)
<223> OTHER INFORMATION: 2'-O-methyluridine (um)
<220> FEATURE:
<221> NAME/KEY: modified_base
<222> LOCATION: (95)..(95)
<223> OTHER INFORMATION: 2'-O-methylguanosine (gm)

<400> SEQUENCE: 5
ugguaucuua caggaacucc guuuuagagc uagaaauagc aaguuaaaau aaggcuaguc 60
cguuaucaac uugaaaaagu ggcaccgagu cggugc 96

<210> SEQ ID NO 6
<211> LENGTH: 96
<212> TYPE: RNA
<213> ORGANISM: Artificial Sequence
<220> FEATURE:
<223> OTHER INFORMATION: hEx45#23 gRNA
<220> FEATURE:
<221> NAME/KEY: modified_base
<222> LOCATION: (1)..(1)
<223> OTHER INFORMATION: 2'-O-methyladenosine
<220> FEATURE:
<221> NAME/KEY: modified_base
<222> LOCATION: (2)..(2)

<223> OTHER INFORMATION: 2'-O-methylguanosine (gm)
<220> FEATURE:
<221> NAME/KEY: modified_base
<222> LOCATION: (3)..(3)
<223> OTHER INFORMATION: 2'-O-methylcytidine (cm)
<220> FEATURE:
<221> NAME/KEY: modified_base
<222> LOCATION: (93)..(93)
<223> OTHER INFORMATION: 2'-O-methylguanosine (gm)
<220> FEATURE:
<221> NAME/KEY: modified_base
<222> LOCATION: (94)..(94)
<223> OTHER INFORMATION: 2'-O-methyluridine (um)
<220> FEATURE:
<221> NAME/KEY: modified_base
<222> LOCATION: (95)..(95)
<223> OTHER INFORMATION: 2'-O-methylguanosine (gm)

<400> SEQUENCE: 6
agcugucaga cagaaaaaag guuuuagagc uagaaauagc aaguuaaaau aaggcuaguc 60
cguuaucaac uugaaaaagu ggcaccgagu cggugc 96

<210> SEQ ID NO 7
<211> LENGTH: 20
<212> TYPE: DNA
<213> ORGANISM: Mus musculus

<400> SEQUENCE: 7
atgaatgtgc ctacatatgg 20

<210> SEQ ID NO 8
<211> LENGTH: 20
<212> TYPE: DNA
<213> ORGANISM: Mus musculus

<400> SEQUENCE: 8
catagcatgc atttggcttc 20

<210> SEQ ID NO 9
<211> LENGTH: 20
<212> TYPE: DNA
<213> ORGANISM: Mus musculus

<400> SEQUENCE: 9
gaatgaggta gtgttgtagg 20

<210> SEQ ID NO 10
<211> LENGTH: 20
<212> TYPE: DNA
<213> ORGANISM: Mus musculus

<400> SEQUENCE: 10
gcaggaaatc atcttatagc 20

<210> SEQ ID NO 11
<211> LENGTH: 120
<212> TYPE: DNA
<213> ORGANISM: Artificial Sequence
<220> FEATURE:
<223> OTHER INFORMATION: ssODN

<400> SEQUENCE: 11
gagcaagctg ggttagaaca aaggtctgtc agagtcagca tgggaatgag gtagtgttgt 60
agcaggaaat agtgtggttt aggtctctcc ccgccctctg tgtatgtgtg tgtgtgtgtt 120

<210> SEQ ID NO 12
<211> LENGTH: 35
<212> TYPE: DNA
<213> ORGANISM: Artificial Sequence
<220> FEATURE:
<223> OTHER INFORMATION: Forward primer

<400> SEQUENCE: 12
ctccgaggcg gatcacaagc aataataacc tgtag 35

<210> SEQ ID NO 13
<211> LENGTH: 35
<212> TYPE: DNA
<213> ORGANISM: Artificial Sequence
<220> FEATURE:
<223> OTHER INFORMATION: Reverse primer

<400> SEQUENCE: 13
tgcaagcacg tttccgactt gagttgcctc aagag 35

<210> SEQ ID NO 14
<211> LENGTH: 20
<212> TYPE: DNA
<213> ORGANISM: Artificial Sequence
<220> FEATURE:
<223> OTHER INFORMATION: mEx43-46skipTaqF114

<400> SEQUENCE: 14
cgtggcacag atggatttcc 20

<210> SEQ ID NO 15
<211> LENGTH: 25
<212> TYPE: DNA
<213> ORGANISM: Artificial Sequence
<220> FEATURE:
<223> OTHER INFORMATION: mEx43-46skipTaqR191

<400> SEQUENCE: 15
ttcttttgtt cttcaatccc ttgtc 25

<210> SEQ ID NO 16
<211> LENGTH: 22
<212> TYPE: DNA
<213> ORGANISM: Artificial Sequence
<220> FEATURE:
<223> OTHER INFORMATION: FAM label, mEx43-46skipTaqP144

<400> SEQUENCE: 16
acttcataga atgtacaagg aa 22

<210> SEQ ID NO 17
<211> LENGTH: 25
<212> TYPE: DNA
<213> ORGANISM: Artificial Sequence
<220> FEATURE:
<223> OTHER INFORMATION: hEx45 TaqF252

<400> SEQUENCE: 17
tcctcaaaaa cagatgccag tattc 25

<210> SEQ ID NO 18
<211> LENGTH: 18
<212> TYPE: DNA
<213> ORGANISM: Artificial Sequence
<220> FEATURE:
<223> OTHER INFORMATION: hEx45 TaqR316

-continued

```
<400> SEQUENCE: 18

tcctgccacc gcagattc                                                18


<210> SEQ ID NO 19
<211> LENGTH: 19
<212> TYPE: DNA
<213> ORGANISM: Artificial Sequence
<220> FEATURE:
<223> OTHER INFORMATION: FAM label, hEx45 TaqP278

<400> SEQUENCE: 19

acaggaaaaa ttgggaagc                                               19
```

DRUG DELIVERY SYSTEM USING SOLUTION

CROSS-REFERENCE TO RELATED APPLICATIONS

This application is the U.S. National Stage of PCT/JP2019/046777, filed Nov. 29, 2019, which claims priority to JP 2018-224965, filed Nov. 30, 2018.

The instant application contains a Sequence Listing which has been submitted in ASCII format via EFS-WEB and is hereby incorporated by reference in its entirety. Said ASCII copy, created on May 27, 2021, is named sequence.txt and is 7,239 bytes.

TECHNICAL FIELD

The present invention relates to a solution for use in delivering and transducing a molecule(s) of interest (e.g., nucleic acid, protein) into a cell. The present invention further relates to a method for transducing a molecule(s) of interest into a cell using the solution and a method for producing a cell having a molecule(s) of interest transduced therein.

BACKGROUND OF THE INVENTION

Various delivery systems to cells have been investigated in the technical field in order to efficiently transfect a nucleic acid, a protein or a complex of these and the like into a cell.

Patent Literature 1 discloses a transduction buffer containing (i) a compound for transduction, (ii) a salt or an activator/enhancer of a sodium-hydrogen transporter and preferably (iii) an osmoprotectant. As the compound for transduction, e.g., betaine (e.g., non-surfactant, sulfo-betaine) and GABA (γ-aminobutyric acid) are disclosed. The literature also discloses in Examples that when KBM7 cells are transduced with gRNA and Cas9 protein, WDR85 gene was cleaved.

Non-patent literature 1 discloses that WDR85 gene was cleaved by transducing a sgRNA-Cas9 protein complex by use of predetermined compounds (e.g., GABA and a non-detergent, sulfobetaine 201 (NDSB-201)) described in Patent Literature 1.

Patent Literature 2 discloses a transduction buffer containing (i) a compound for transduction, (ii) 250 to 2500 mM of at least one salt (Na, Rb, Li, K or Cs), (iii) an osmotic pressure inducer (osmotic pressure: 500 to 5000 mOsmol/kg) and (iv) an osmoprotectant. The literature also discloses in Examples that a target gene was cleaved by transducing gRNA and Cas9 protein into KBM7 cells.

Non Patent Literature 2 discloses that a target gene was cleaved by addition of one to four SV40 NLSs to the N terminal of Cas9 protein and transduction of a complex of the Cas9/gRNA in vitro (neural progenitor cells) and in vivo (mouse brain by injection).

CITATION LIST

Patent Literatures

Patent Literature 1: International Publication No. WO2015/028969

Patent Literature 2: International Publication No. WO 2017/093326

Non Patent Literatures

Non Patent Literature 1: D'Astolfo et al., Cell, 161, 674-690, Apr. 23, 2015

Non Patent Literature 2: Brett T Staahl et al., Nature Biotechnology, 35, 431-434, 2017

SUMMARY OF INVENTION

Technical Problem

An object of the present invention is to provide a means excellent in efficiency of introduction of a nucleic acid, a protein, a complex thereof, or the like into cells, in particular a method using a solution for transduction. In another aspect, an object of the present invention is to provide a method for producing transduced cells using the means.

Solution to Problem

The present inventors conducted intensive studies with a view to attaining the above objects. As a result, they have found that a nucleic acid, a protein or a complex of these can be highly efficiently introduced into a cell using a solution of a predetermined compound or molecule, thereby attaining the objects. Based on the finding, the present invention was accomplished.

The present invention at least relates to the following inventions.

[1]

A method for transducing a molecule(s) of interest into a cell, comprising a step of contacting the cell with the molecule(s) of interest and a solution for transduction, wherein the solution for transduction comprises at least one of the following (A1) to (A5); and (B) a salt:

(A1) a compound represented by the following formula (I), or a salt thereof, excluding 20 L-amino acids serving as structural units of a biological protein and S-methyl-L-methionine:

[Formula 1]

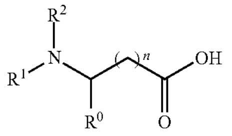

I wherein n is 0 or 1, $R^1$ and $R^2$ each independently represent a hydrogen atom or $COR^3$, $R^0$ represents a side chain, excluding a $C_{1-6}$ alkyl group, constituting an amino acid serving as a structural unit of a biological protein optionally having a $C_{1-6}$ alkyl group that optionally has a substituent, provided that if $R^0$ is a hydrogen atom, $R^1$ represents $COR^3$ and $R^2$ represents a hydrogen atom, wherein $R^3$ represents a $C_{1-6}$ alkyl group (excluding a methyl group) optionally having a substituent (excluding a thiol group and a disulfide group); or $NR^4R^5$, wherein $R^4$ and $R^5$ each independently represent a hydrogen atom or a $C_{1-4}$ alkyl group;

(A2) a compound represented by following formula (II), or a salt thereof:

[Formula 2]

II

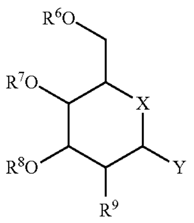

wherein X represents an oxygen atom or $NR^{11}$, wherein $R^{11}$ represents a hydrogen atom, a $C_{1-4}$ alkyl group optionally having a substituent; or $COR^{12}$, wherein $R^{12}$ represents a $C_{1-6}$ alkyl group, Y represents a hydrogen atom or $OR^{10}$, $R^6$, $R^7$, $R^8$ and $R^{10}$ each independently represent a hydrogen atom or a phosphonic acid group, $R^9$ represents a hydrogen atom, a hydroxy group or a is phosphoric group, when $R^{10}$ is a hydrogen atom, at least one of $OR^6$, $OR^7$, $OR^8$ and $R^9$ is a phosphoric group;

provided that the compound represented by formula (II) includes a compound having a chain structure, which is in chemical equilibrium with a compound represented by formula (II) in an aqueous solution;

(A3) a nucleic-acid base, a nucleoside or a nucleotide, or a salt thereof;

(A4) a compound represented by formula (III), or a salt thereof, excluding malic acid:

Rx-CRyRzCOOH III wherein Rx represents a linear $C_{2-4}$ alkyl group substituted with at least one selected from the group consisting of a $C_{1-6}$ alkyl group, an optionally substituted hydroxy group, an oxo group and a carboxyl group, Ry and Rz each independently represent a hydrogen atom is or a hydroxy group (provided that at least one of them is a hydroxy group), or are taken together to represent an oxo group; and (A5) at least one selected from the group consisting of creatinine, hydroxyproline, 1,3-butanediol, trientine, D-cellobiose, 1,3-dimethylurea, pantolactone and trimethadione, or a salt thereof.

[2] The method according to item 1, wherein (A1) is a compound selected from argininosuccinic acid, 1-methyl-L-histidine, pantothenic acid, L-carnosine and N-carbamyl-L-aspartic acid, or a salt thereof;

(A2) is a compound selected from miglitol, 2-deoxy-D-glucose-6-phosphate, α-D-glucose 1-phosphate and 1-deoxynojirimycin, or a salt thereof;

(A3) is a compound selected from cytosine, cytidine, deoxyuridine, deoxycytidine and 5'-inosinic acid, or a salt thereof;

(A4) is a compound selected from 6-phospho-D-gluconic acid, 3-methyl-2-oxobutanoic acid and 2-hydroxyglutaric acid, or a salt thereof; and (A5) is a compound selected from creatinine, hydroxyproline, 1,3-butanediol, 1,3-dimethylurea, D-cellobiose, 1,3-dimethylurea, pantolactone and trimethadione, or a salt thereof.

[3] The method according to item 1, wherein the at least one of (A1) to (A5) is a compound selected from 1-methyl-L-histidine, N-carbamyl-L-aspartic acid, deoxycytidine, 2-deoxy-D-glucose-6-phosphate and 6-phospho-D-gluconic acid, or a salt thereof.

[4] The method according to item 1, wherein the (B) salt is at least one selected from the group consisting of sodium chloride, magnesium chloride and potassium chloride.

[5] The method according to item 1, wherein the molecule(s) of interest includes a protein and/or a nucleic acid.

[6] The method according to item 1, wherein the molecule(s) of interest includes a Cas protein and/or gRNA.

[7] The method according to item 1, wherein the cell is present in a living body.

[8] The method according to item 1, wherein the cell is a muscle cell.

[9] A method for producing a cell having a molecule(s) of interest transduced therein, comprising a step of contacting the cell with a molecule(s) of interest and a solution for transduction, wherein the solution for transduction comprises: at least one of the following (A1) to (A5); and (B) a salt:

(A1) a compound represented by the following formula (I), or a salt thereof, excluding 20 L-amino acids serving as structural units of a biological protein and S-methyl-L-methionine:

[Formula 3]

I

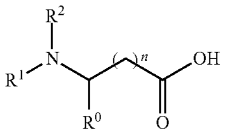

wherein n is 0 or 1, $R^1$ and $R^2$ each independently represent a hydrogen atom or $COR^3$, $R^0$ represents a side chain, excluding a $C_{1-6}$ alkyl group, constituting an amino acid serving as a structural unit of a biological protein optionally having a $C_{1-6}$ alkyl group that optionally has a substituent, provided that if $R^0$ is a hydrogen atom, $R^1$ represents $COR^3$ and $R^2$ represents a hydrogen atom, wherein $R^3$ represents a $C_{1-6}$ alkyl group (excluding a methyl group) optionally having a substituent (excluding a thiol group and a disulfide group); or $NR^4R^5$, wherein $R^4$ and $R^5$ each independently represent a hydrogen atom or a $C_{1-4}$ alkyl group;

(A2) a compound represented by the following formula (II), or a salt thereof:

[Formula 4]

II

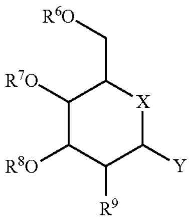

wherein X represents an oxygen atom or $NR^{11}$, wherein $R^{11}$ represents a hydrogen atom, a $C_{1-4}$ alkyl group optionally having a substituent; or $COR^{12}$, wherein $R^{12}$ represents a $C_{1-6}$ alkyl group, Y represents a hydrogen atom or $OR^{10}$, $R^6$, $R^7$, $R^8$ and $R^{10}$ each independently represent a hydrogen atom or a phosphonic acid group, $R^9$ represents a hydrogen atom, a hydroxy group or a phosphoric group, when $R^{10}$ is a hydrogen atom, at least one of $OR^6$, $OR^7$, $OR^8$ and $R^9$ is a phosphoric group;

provided that the compound represented by formula (II) includes a compound having a chain structure, which is in chemical equilibrium with a compound represented by formula (II) in an aqueous solution, (A3) a nucleic-acid base, a nucleoside or a nucleotide, or a salt thereof;

(A4) a compound represented by formula (III), or a salt thereof excluding malic acid:

Rx-CRyRzCOOH III wherein Rx represents a linear $C_{2-4}$ alkyl group substituted with at least one selected from the group consisting of a $C_{1-6}$ alkyl group, an optionally substituted hydroxy group, an oxo group and a carboxyl group, Ry and Rz each independently represent a hydrogen atom or a hydroxy group (provided that at least one of them is a hydroxy group) or are taken together to represent an oxo group; and (A5) at least one selected from the group consisting of creatinine, hydroxyproline, 1,3-butanediol, trientine, D-cellobiose, 1,3-dimethylurea, pantolactone and trimethadione, or a salt thereof.

[10] The method according to item 9, wherein (A1) is a compound selected from argininosuccinic acid, 1-methyl-L-histidine, pantothenic acid, L-carnosine and N-carbamyl-L-aspartic acid, or a salt thereof;

(A2) is a compound selected from miglitol, 2-deoxy-D-glucose-6-phosphate, α-D-glucose 1-phosphate and 1-deoxynojirimycin, or a salt thereof;

(A3) is a compound selected from cytosine, cytidine, deoxyuridine, deoxycytidine and 5'-inosinic acid, or a salt thereof;

(A4) is a compound selected from 6-phospho-D-gluconic acid, 3-methyl-2-oxobutanoic acid and 2-hydroxyglutaric acid, or a salt thereof, (A5) is a compound selected from creatinine, hydroxyproline, 1,3-butanediol, 1,3-dimethylurea, D-cellobiose, 1,3-dimethylurea, pantolactone and trimethadione, or a salt thereof.

[11] The method according to item 9, wherein the at least one of (A1) to (A5) is a compound selected from 1-methyl-L-histidine, N-carbamyl-L-aspartic acid, deoxycytidine, 2-deoxy-D-glucose-6-phosphate and 6-phospho-D-gluconic acid, or a salt thereof.

[12] The method according to item 9, wherein the (B) salt is at least one selected from the group consisting of sodium chloride, magnesium chloride and potassium chloride.

[13] The method according to item 9, wherein the molecule(s) of interest includes a protein and/or a nucleic acid.

[14] The method according to item 9, wherein the molecule(s) of interest includes a Cas protein and/or gRNA.

[15] The method according to item 9, wherein the cell is present in a living body.

[16] The method according to item 9, wherein the cell is a muscle cell.

[17] A solution for transduction comprising: at least one of the following (A1) to (A5); and (B) a salt:

(A1) a compound represented by the following formula (I), or a salt thereof, excluding 20 L-amino acids serving as structural units of a biological protein and S-methyl-L-methionine:

[Formula 5]

I

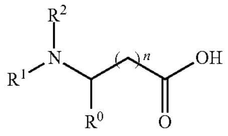

wherein n is 0 or 1, $R^1$ and $R^2$ each independently represent a hydrogen atom or $COR^3$, $R^0$ represents a side chain, excluding a $C_{1-6}$ alkyl group, constituting an amino acid serving as a structural unit of a biological protein optionally having a $C_{1-6}$ alkyl group that optionally has a substituent, provided that if $R^0$ is a hydrogen atom, $R^1$ represents $COR^3$ and $R^2$ represents a hydrogen atom, wherein $R^3$ represents a $C_{1-6}$ alkyl group (excluding a methyl group) optionally having a substituent (excluding a thiol group and a disulfide group); or $NR^4R^5$, wherein $R^4$ and $R^5$ each independently represent a hydrogen atom or a $C_{1-4}$ alkyl group;

(A2) a compound represented by the following formula (II), or a salt thereof:

[Formula 6]

II

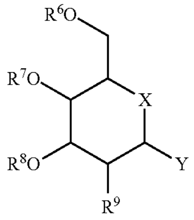

wherein X represents an oxygen atom or $NR^{11}$, wherein $R^{11}$ represents a hydrogen atom, a $C_{1-4}$ alkyl group optionally having a substituent; or $COR^{12}$, wherein $R^{12}$ represents a $C_{1-6}$ alkyl group, Y represents a hydrogen atom or $OR^{10}$, $R^6$, $R^7$, $R^8$ and $R^{10}$ each independently represent a hydrogen atom or a phosphonic acid group, $R^9$ represents a hydrogen atom, a hydroxy group or a phosphoric group, when $R^{10}$ is a hydrogen atom, at least one of $OR^6$, $OR^7$, $OR^8$ and $R^9$ is a phosphoric group;

provided that the compound represented by formula (II) includes a compound having a chain structure, which is in chemical equilibrium with a compound represented by formula (II) in an aqueous solution;

(A3) a nucleic-acid base, a nucleoside or a nucleotide, or a salt thereof;

(A4) a compound represented by formula (III), or a salt thereof, excluding malic acid:

Rx-CRyRzCOOH III wherein Rx represents a linear $C_{2-4}$ alkyl group substituted with at least one selected from the group consisting of a $C_{1-6}$ alkyl group, an optionally substituted hydroxy group, an oxo group and a carboxyl group, Ry and Rz each independently represent a hydrogen atom or a hydroxy group (provided that at least one of them is a hydroxy group), or are taken together to represent an oxo group; and (A5) at least one selected from the group consisting of creatinine, hydroxyproline, 1,3-butanediol, trientine, D-cellobiose, 1,3-dimethylurea, pantolactone and trimethadione, or a salt thereof.

[18] The solution for transduction according to item 17, wherein (A1) is a compound selected from argininosuccinic acid, 1-methyl-L-histidine, pantothenic acid, L-carnosine and N-carbamyl-L-aspartic acid, or a salt thereof;

(A2) is a compound selected from miglitol, 2-deoxy-D-glucose-6-phosphate, α-D-glucose 1-phosphate and 1-deoxynojirimycin, or a salt thereof;

(A3) is a compound selected from cytosine, cytidine, deoxyuridine, deoxycytidine and 5'-inosinic acid, or a salt thereof;

(A4) is a compound selected from 6-phospho-D-gluconic acid, 3-methyl-2-oxobutanoic acid and 2-hydroxyglutaric acid, or a salt thereof; and (A5) is a compound selected from creatinine, hydroxyproline, 1,3-butanediol, 1,3-dimethylurea, D-cellobiose, 1,3-dimethylurea, pantolactone and trimethadione, or a salt thereof.

[19] The solution for transduction according to item 17, wherein the at least one of (A1) to (A5) is a compound selected from 1-methyl-L-histidine, N-carbamyl-L-aspartic acid, deoxycytidine, 2-deoxy-D-glucose-6-phosphate and 6-phospho-D-gluconic acid, or a salt thereof.

[20] The solution for transduction according to item 17, wherein the (B) salt is at least one selected from the group consisting of sodium chloride, magnesium chloride and potassium chloride.

[21] A pharmaceutical composition comprising the solution for transduction according to item 17 and a molecule(s) of interest.

[22] The pharmaceutical composition according to item 21, wherein the molecule(s) of interest includes a protein and/or nucleic acid.

[23] The pharmaceutical composition according to item 21, wherein the molecule(s) of interest includes a Cas protein and/or gRNA.

As used herein, "a compound represented by formula (I)", "a compound represented by formula (II)" and "a compound represented by formula (III)" will be sometimes referred to as a "compound (I)", a "compound (II)" and a "compound (III)", respectively. The compounds described in the (A1) to (A5) and the salts thereof will be sometimes referred to as a "compound (A1)" to a "compound (A5)", respectively. At least one of the following (A1) to (A5), and (B) a salt will be sometimes referred to as "components (A1) to (A5) and (B)".

Advantageous Effects of Invention

The transduction method of the present invention makes it possible to highly efficiently introduce a nucleic acid, a protein or a complex of these and the like into a cell. For example, if a complex of gRNA and Cas9 protein used in the CRISPR system is highly efficiently introduced into a cell in accordance with the transduction method of the present invention, high DNA cleavage activity by the CRISPR system can be achieved. Use of the transduction method of the present invention enables efficient production of a transduced cell.

BRIEF DESCRIPTION OF DRAWINGS

FIG. 1 shows a reporter cassette to establish EGFP a reporter cell.

FIG. 2 shows results of image analysis of EGFP reporter cells stained with EGFP and HOECHST and scanned by visible light.

FIG. 3 shows the expression site of Cas9 protein.

FIG. 4-1 FIG. 4 (FIG. 4-1 and FIG. 4-2) each show the determination results of the EGFP-positive rate and the number of HOECHST cells when compounds (A1) to (A5) were used at different concentrations (see, Example 1).

FIG. 4-2 As described above.

FIG. 5 shows the determination results of the EGFP-positive rate and the number of HOECHST cells when compounds (A1) to (A5) were each used at a predetermined concentration (see, Example 1).

FIG. 6 shows the determination results of the EGFP-positive rate and the number of HOECHST cells when compounds (A1) to (A5) were each used at a predetermined concentration (see, Example 2).

FIG. 7 shows the determination results of the EGFP-positive rate and the number of HOECHST cells when the (B) salts were used at different concentrations (see, Example 3).

FIG. 8 shows the determination results of the EGFP-positive rate when compounds (A1) to (A5) were used at a variety of concentrations of sodium chloride as the (B) salt (see, Example 4).

FIG. 9 shows the determination results of the mutation introduction efficiency (indel (%)) when an administration solution (administration solution 1) containing 2'-deoxycytidine as compound (A3), sodium chloride different in concentration and a complex of mRosa26 gRNA and Cas9 protein, was locally administered in the mouse right lower limb gastrocnemius (see, Example 5).

FIG. 10 shows the determination results of the mutation introduction efficiency (indel (%)) when an administration solution (administration solution 2) containing a compound of any one of (A1) to (A5), sodium chloride, and a complex of mRosa26 gRNA and Cas9 protein, was locally administered in the mouse right lower limb gastrocnemius (see, Example 6).

FIG. 11 shows the determination results of skipping efficiency (%) when an administration solution (administration solution 3) containing 6-phospho-D-gluconic acid or N-carbamyl-L-aspartic acid different in concentration, sodium chloride and a complex of mRosa26 gRNA and Cas9 protein, was locally administered to the mouse tibialis anterior muscle (see, Example 7).

FIG. 12 shows fluorescence micrographs for evaluating intracellular uptake of fluorescent-labeled dextran, which was carried out by use of a solution for transduction containing 6-phospho-D-gluconic acid or N-carbamyl-L-aspartic acid (GABA used as a control) and sodium chloride (see, Example 8). A bright portions in the fluorescence micrographs indicate fluorescent-labeled dextran taken in cells.

DESCRIPTION OF EMBODIMENTS

As used herein, "transduction" (transfection) refers to introducing any substance inside a cell. The "inside a cell" at least include "inside the cytoplasm" and "inside a nucleus".

The term "culture" or "to culture" means that cells are maintained outside a tissue or a body, for example, in a dish, a petri dish, a flask or a culture vessel (tank), proliferated and/or differentiated.

The term "comprise(s)" or "comprising" means that the elements following the term are included but the elements are non-limiting elements. Accordingly, it is suggested that the elements following the term are included and not suggested that any other elements are excluded.

The term "consist(s) of" or "consisting of" means that the elements following the term are all included and the elements are limiting. Accordingly, the term "consist of" means that the elements listed up are required or essential and other elements are substantially not present. The phrase "essentially consist of" means that any elements following the phrase are included and the elements are limited to other elements having no effect on the activity or action specified by the disclosure of the invention. Accordingly, the phrase "essentially consist of" means that the elements listed up are required or essential and the other elements are optional, and whether the other elements are allowed to be present or not is determined depending on whether they have an effect on the activity or action of the elements listed up.

As used herein, the clustered regularly interspersed short palindromic repeats (CRISPR)/CRISPR-associated (Cas) system will be referred to as "CRISPR system".

Now, individual substituents to be used herein will be defined, below. Unless otherwise specified, individual substituents are defined as follows.

As used herein, the "$C_{1-4}$ alkyl group" includes methyl, ethyl, propyl, isopropyl, butyl, isobutyl, sec-butyl, and tert-butyl.

As used herein, the "$C_{1-6}$ alkyl group" includes methyl, ethyl, propyl, isopropyl, butyl, isobutyl, sec-butyl, tert-butyl, pentyl, isopentyl, neopentyl, 1-ethyl propyl, hexyl, isohexyl, 1,1-dimethylbutyl, 2,2-dimethylbutyl, 3,3-dimethylbutyl and 2-ethylbutyl.

As used herein, the "linear $C_{2-4}$ alkyl group" includes ethyl, propyl and butyl.

As used herein, the "substituent" which a $C_{1-6}$ alkyl group or $C_{1-4}$ alkyl group optionally has includes a $C_{1-6}$ alkyl group, a hydroxy group, an amino group and a carboxyl group. Unless otherwise specified herein, a $C_{1-6}$ alkyl group or $C_{1-4}$ alkyl group may have a single substituent or a plurality of substituents independent of each other at substitution-possible sites.

Now, the solution for transduction of the present invention will be more specifically described.

The solution for transduction of the present invention contains: at least one of the following (A1) to (A5); and (B) a salt.

Compounds (A1) are represented by the following formula (I), or salts thereof, excluding 20 L-amino acids serving as structural units of a biological protein and S-methyl-L-methionine. Compounds (A1) may be hydrates. Compounds (A1) may be used alone or in combination of two or more.

[Formula 7]

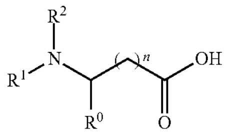

I

In the formula (I), n is 0 or 1, $R^1$ and $R^2$ each independently represent a hydrogen atom or $COR^3$, $R^0$ represents a side chain, excluding a $C_{1-6}$ alkyl group, constituting an amino acid serving as a structural unit of a biological protein optionally having a $C_{1-6}$ alkyl group that optionally has a substituent, provided that if $R^0$ is a hydrogen atom, $R^1$ represents $COR^3$ and $R^2$ represents a hydrogen atom, wherein $R^3$ represents a $C_{1-6}$ alkyl group (excluding a methyl group) optionally having a substituent (excluding a thiol group and a disulfide group); or $NR^4R^5$, wherein $R^4$ and $R^5$ each independently represent a hydrogen atom or a $C_{1-4}$ alkyl group.

Note that, the definition of $R^0$: "side chain constituting an amino acid serving as a structural unit of a biological protein" does not include a ring (pyrrolidine), which constitutes a part of pyrroline and formed together with a carbon atom to which $R^0$ is bound and a nitrogen atom to which $R^1$ is bound.

In formula (I), preferable examples of each of n, $R^1$, $R^2$, $R^3$, $R^0$, $R^4$ and $R^5$ are as follows.

n is preferably 0 or 1.

$R^1$ is preferably a hydrogen atom or $COR^3$.

$R^2$ is preferably a hydrogen atom.

$R^3$ is preferably a $C_{1-6}$ alkyl group (excluding a methyl group) optionally having a substituent (excluding a thiol group and a disulfide group); or $NR^4R^5$.

$R^0$ is preferably a hydrogen atom or a side chain constituting arginine, histidine, aspartic acid, asparagine, glutamic acid, glutamine, ricin, phenylalanine, serine, threonine, tryptophan, tyrosine, cysteine or methionine optionally having a $C_{1-6}$ alkyl group that optionally has a substituent.

$R^4$ is preferably a hydrogen atom or a $C_{1-4}$ alkyl group.

$R^5$ is preferably a hydrogen atom or a $C_{1-4}$ alkyl group.

Preferred examples of the compound (I) are as follows. The following compounds may be salts and/or hydrates.

Compound (I-i): a compound wherein n is 0 or 1; $R^1$ is a hydrogen atom or $COR^3$; $R^2$ is a hydrogen atom; $R^3$ is a $C_{1-6}$ alkyl group (excluding a methyl group) optionally having a substituent (excluding a thiol group and a disulfide group); and $R^0$ is a hydrogen atom or a side chain constituting arginine, histidine, aspartic acid, asparagine, glutamic acid, glutamine, ricin, phenylalanine, serine, threonine, tryptophan, tyrosine, cysteine or methionine optionally having a $C_{1-6}$ alkyl group optionally having a substituent.

Compound (I-ii): a compound wherein n is 0 or 1; $R^1$ is $COR^3$; $R^2$ is a hydrogen atom; $R^3$ is a $C_{1-6}$ alkyl group (excluding a methyl group) optionally having a substituent (excluding a thiol group and a disulfide group); and $R^0$ is a hydrogen atom or a side chain constituting arginine, histidine, aspartic acid, asparagine, glutamic acid, glutamine, ricin, phenylalanine, serine, threonine, tryptophan, tyrosine, cysteine or methionine optionally having a $C_{1-6}$ alkyl group optionally having a substituent.

Compound (I-iii): a compound wherein n is 0 or 1; $R^1$ is $COR^3$; $R^2$ is a hydrogen atom; $R^3$ is $NR^4R^5$; $R^0$ is a hydrogen atom or a side chain constituting arginine, histidine, aspartic acid, asparagine, glutamic acid, glutamine, ricin, phenylalanine, serine, threonine, tryptophan, tyrosine, cysteine or methionine optionally having a $C_{1-6}$ alkyl group optionally having a substituent; $R^4$ is a hydrogen atom; and $R^5$ is a hydrogen atom.

More preferred examples of the compound (I) are as follows. The following compounds may be salts and/or hydrates.

Compound (I-a): a compound wherein n is 0, $R^1$ is a hydrogen atom; $R^2$ is a hydrogen atom; $R^0$ is a side chain constituting arginine optionally having a $C_{1-6}$ alkyl group that optionally has a substituent; for example, argininosuccinic acid.

Compound (I-b): a compound wherein n is 0; $R^1$ is a hydrogen atom; $R^2$ is a hydrogen atom; and $R^0$ is a side chain constituting histidine optionally having a $C_{1-6}$ alkyl group; for example, 1-methyl-L-histidine.

Compound (I-c): a compound wherein n is 1; $R^1$ is $COR^3$; $R^2$ is a hydrogen atom; $R^3$ is a $C_{1-6}$ alkyl group or a propyl group optionally having a hydroxy group; and $R^0$ is a hydrogen atom; for example, pantothenic acid.

Compound (I-d): a compound wherein n is 0; $R^1$ is $COR^3$; $R^2$ is a hydrogen atom; $R^3$ is an ethyl group optionally having an amino group; and $R^0$ is a side chain constituting histidine optionally having a $C_{1-6}$ alkyl group; for example, L-carnosine.

Compound (I-e): a compound wherein n is 0; $R^1$ is $COR^3$; $R^2$ is a hydrogen atom; $R^3$ is $NR^4R^5$; $R^0$ is a side chain constituting aspartic acid optionally having a $C_{1-6}$ alkyl group; $R^4$ is a hydrogen atom; and $R^5$ is a hydrogen atom; for example, N-carbamyl-L-aspartic acid (sometimes also referred to as N-carbamoyl-L-aspartic acid).

In an aspect of the present invention, (A1) may be a compound selected from argininosuccinic acid, 1-methyl-L-histidine, pantothenic acid, L-carnosine and N-carbamyl-L-aspartic acid, or a salt thereof (which may be a hydrate); and, of them particularly preferably, a compound selected from argininosuccinic acid, 1-methyl-L-histidine, L-carnosine and N-carbamyl-L-aspartic acid, or a salt thereof (which may be a hydrate).

In another aspect of the present invention, (A1) is particularly preferably a compound selected from 1-methyl-L-histidine and N-carbamyl-L-aspartic acid, or a salt thereof (which may be a hydrate).

The compounds (A2) are compounds represented by the following formula (II), or salts thereof. The compounds (A2) may be hydrates. Compounds (A2) may be used alone or in combination of two or more.

[Formula 8]

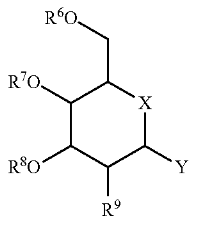

II

In formula (II),

X represents an oxygen atom or $NR^{11}$, wherein $R^{11}$ represents a hydrogen atom, a $C_{1-4}$ alkyl group optionally having a substituent; or $COR^{12}$, wherein $R^{12}$ represents a $C_{1-6}$ alkyl group, Y represents a hydrogen atom or $OR^{10}$, $R^6$, $R^7$, $R^8$ and $R^{10}$ each independently represent a hydrogen atom or a phosphonic acid group ($—P(=O)(OH)_2$), $R^9$ represents a hydrogen atom, a hydroxy group or a phosphoric group ($—O—P(=O)(OH)_2$), and when $R^{10}$ is a hydrogen atom, at least one of $OR^6$, $OR^7$, $OR^8$ and $R^9$ is a phosphoric group, provided that the compound represented by formula (II) includes a compound having a chain structure, which is in the state of chemical equilibrium with a compound represented by formula (II) in an aqueous solution.

Preferred examples of each of X, Y, $R^{11}$, $R^6$, $R^7$, $R^8$, $R^9$ and $R^{10}$ in formula (II) are as follows:

X is preferably an oxygen atom or $NR^{11}$.

Y is preferably a hydrogen atom or $OR^{10}$.

$R^{11}$ is preferably a hydrogen atom or a $C_{1-4}$ alkyl group optionally having a substituent.

$R^6$ is preferably a hydrogen atom or a phosphonic acid group.

$R^7$ is preferably a hydrogen atom or a phosphonic acid group.

$R^8$ is preferably a hydrogen atom or a phosphonic acid group.

$R^9$ is preferably a hydrogen atom, a hydroxy group or a phosphoric group.

$R^{10}$ is preferably a hydrogen atom or a phosphonic acid group.

Preferred examples of the compound (II) are as follows. The compounds listed below may be salts and/or hydrates.

Compound (II-i): a compound wherein X is $NR^{11}$; Y is a hydrogen atom; $R^6$ is a hydrogen atom or a phosphonic acid group; $R^7$ is a hydrogen atom or a phosphonic acid group; $R^8$ is a hydrogen atom or a phosphonic acid group; $R^9$ is a hydroxy group or a phosphoric group; $R^{10}$ is a hydrogen atom or a phosphonic acid group; and $R^{11}$ is a hydrogen atom or a $C_{1-4}$ alkyl group optionally having a substituent.

Compound (II-ii): a compound wherein X is an oxygen atom; Y is $OR^{10}$; $R^6$ is a hydrogen atom or a phosphonic acid group; $R^7$ is a hydrogen atom or a phosphonic acid group; $R^8$ is a hydrogen atom or a phosphonic acid group; $R^9$ is a hydrogen atom, a hydroxy group or a phosphoric group; and $R^{10}$ is a hydrogen atom or a phosphonic acid group.

More preferred examples of the compound (II) are as follows. The following compounds may be salts and/or hydrates.

Compound (II-a): a compound wherein X is $NR^{11}$; Y is a hydrogen atom; $R^6$ is a hydrogen atom; $R^7$ is a hydrogen atom; $R^8$ is a hydrogen atom; $R^9$ represents a hydroxy group; and $R^{11}$ is a 2-hydroxyethyl group; for example, miglitol.

Compound (II-b): a compound wherein X is an oxygen atom; Y is $OR^{10}$; $R^6$ represents a phosphoric group; $R^7$ is a hydrogen atom; $R^8$ is a hydrogen atom; $R^9$ is a hydrogen atom; and $R^{10}$ is a hydrogen atom; for example, 2-deoxy-D-glucose-6-phosphate.

Compound (II-c): a compound wherein X is an oxygen atom; Y is $OR^{10}$; $R^6$ is a hydrogen atom; $R^7$ is a hydrogen atom; $R^8$ is a hydrogen atom; $R^9$ is a hydroxy group; and $R^{10}$ is a phosphonic acid group; for example, α-D-glucose 1-phosphate.

Compound (II-d): a compound wherein X is $NR^{11}$; Y is a hydrogen atom; $R^6$ is a hydrogen atom; $R^7$ is a hydrogen atom; $R^8$ is a hydrogen atom; $R^9$ is a hydroxy group; and $R^{11}$ is a hydrogen atom; for example, 1-deoxynojirimycin.

In an aspect of the present invention, (A2) is particularly preferably a compound selected from miglitol, 2-deoxy-D-glucose-6-phosphate, α-D-glucose 1-phosphate and 1-deoxynojirimycin, or a salt thereof (which may be a hydrate).

In another aspect of the present invention, (A2) is particularly preferably 2-deoxy-D-glucose-6-phosphate, or a salt thereof (which may be a hydrate).

Compounds (A3) are a nucleic-acid base, a nucleoside and a nucleotide, or salts thereof. The compounds (A3) may be hydrates. Compounds (A3) may be used alone or in combination of two or more.

Note that, in an embodiment, a molecule(s) of interest may be a "nucleic acid". The "nucleic acid" is a polynucleotide or an oligonucleotide; whereas, the "nucleotide" serving as the compound (A3) is a mononucleotide or a dinucleotide. In this respect, both are distinguishable.

Examples of the nucleic-acid base include adenine, guanine, cytosine, thymine and uracil, and modified these bases such as methylated cytosine, hydroxymethylated cytosine, methylated guanine, hypoxanthine (deaminated adenine, 6-hydroxyproline), pseudo uracil, dihydrouracil, thiouracil, methylamino selenouracil, taurinomethyluracil, rigisine, agmatinylcytosine, archaeosine, queuosine, wyosine and other modified nucleic-acid bases contained in e.g., genomic DNA, mRNA, tRNA and rRNA.

The nucleoside is a compound formed by binding a ribose or another sugar to a base, and ribonucleoside and deoxyribonucleoside and the like are included. Examples of the ribonucleoside include adenosine, guanosine, cytidine, uridine, 5-methyluridine, and compounds obtained by binding a ribose to other modified nucleic-acid bases mentioned above. Examples of the deoxyribonucleotide include deoxyadenosine, deoxyguanosine, deoxycytidine, thymidine, deoxyuridine, and compounds formed by binding a deoxyribose to other modified nucleic-acid bases mentioned above. Examples of the nucleoside include inosine (a compound formed by binding a ribose to hypoxanthine) and riboflavin (vitamin B2, a compound formed by binding a reduced linear ribose (ribitol) to dimethylisoaroxazine).

The nucleotide is a compound formed by binding a phosphoric group to a sugar residue such as ribonucleoside and deoxyribonucleoside. Examples of the nucleotide include adenosine monophosphate (AMP), adenosine diphosphate (ADP), adenosine triphosphate (ATP), guanosine monophosphate (GMP), guanosine diphosphate (GDP), guanosine triphosphate (GTP), cytidine monophosphate (CMP), cytidine diphosphate (CDP), cytidine triphosphate (CTP), uridine monophosphate (UMP), uridine diphosphate (UDP), uridine triphosphate (UTP) and compounds formed by binding one or more phosphoric groups to other ribonucleosides; and deoxyadenosine monophosphate (dAMP), deoxyadenosine diphosphate (dADP), deoxyadenosine triphosphate (dATP), deoxyguanosine monophosphate (dGMP), deoxyguanosine diphosphate (dGDP), deoxyguanosine triphosphate (dGTP), deoxycytidine monophosphate (dCMP), deoxycytidine diphosphate (dCDP), deoxycytidine triphosphate (dCTP), thymidine monophosphate (dTMP), thymidine diphosphate (dDMP), thymidine triphosphate (dTMP), deoxyuridine monophosphate (dUMP), deoxyuridine diphosphate (dUDP), deoxyuridine triphosphate (dUTP), and compounds formed by binding one or more phosphoric groups to other deoxyribonucleosides. Examples of the nucleotide also include inosinic acid (inosine monophosphate), flavin mononucleotide (FMN) and flavin adenine dinucleotide (FAD). Examples of the nucleotide also include compounds formed by binding a cyclic phosphoric group to a nucleoside, such as cyclic AMP (cAMP) and cyclic GMP (cGMP).

Preferred examples of the compound (A3) are as follows. The following compounds may be salts and/or hydrates.

Nucleic-acid base: adenine, guanine, cytosine, thymine, uracil and hypoxanthine.

Nucleoside: adenosine, guanosine, cytidine, uridine, 5-methyluridine, deoxyadenosine, deoxyguanosine, deoxycytidine, thymidine, deoxyuridine and inosine.

Nucleotide: adenosine monophosphate, guanosine monophosphate, cytidine monophosphate, uridine monophosphate, deoxyadenosine monophosphate, deoxyadenosine diphosphate, deoxyguanosine monophosphate, deoxycytidine monophosphate, deoxycytidine diphosphate, thymidine monophosphate, deoxyuridine monophosphate and inosinic acid.

More preferred examples of the compound (A3) are as follows. The following compounds may be salts and/or hydrates.

Nucleic-acid base: cytosine.

Nucleoside: cytidine, deoxyuridine and deoxycytidine.

Nucleotide: 5'-inosinic acid.

In an aspect of the present invention, (A3) is a compound selected from cytosine, cytidine, deoxyuridine, deoxycytidine, and 5'-inosinic acid, or a salt thereof (which may be a hydrate); and, of them, particularly preferably, a compound selected from cytidine, deoxycytidine and 5'-inosinic acid, or a salt thereof (which may be a hydrate).

In another aspect of the present invention, (A3) is particularly preferably deoxycytidine, or a salt thereof (which may be a hydrate).

Compounds (A4) are compounds represented by formula (III) excluding malic acid, or salts thereof. The compounds (A4) may be hydrates. Compounds (A4) may be used alone or in combination of two or more.

Rx-CRyRzCOOH III

In formula (III),

Rx represents a linear $C_{2-4}$ alkyl group substituted with at least one selected from the group consisting of a $C_{1-6}$ alkyl group, an optionally substituted hydroxy group, an oxo group and a carboxyl group, Ry and Rz each independently represent a hydrogen atom or a hydroxy group (provided that at least one of them is a hydroxy group), or are taken together to represent an oxo group.

Examples of the optionally substituted hydroxy group for Rx include, for example, a hydroxy group optionally substituted with a phosphonic acid group.

Preferred examples of Rx, Ry and Rz in formula (III) are as follows.

Rx is preferably a linear $C_{2-4}$ alkyl group substituted with at least one selected from the group consisting of a $C_{1-6}$ alkyl group, a hydroxy group, a phosphoric group, an oxo group and a carboxyl group.

Ry is preferably a hydroxy group or forms an oxo group together with Rz.

Rz is preferably a hydrogen atom or forms an oxo group together with Ry.

Preferred examples of the compound (III) are as follows.

Compound (III-i): a compound wherein Rx is a linear $C_{2-4}$ alkyl group substituted with at least one group selected from the group consisting of a $C_{1-6}$ alkyl group, a hydroxy group, a phosphoric group, an oxo group and a carboxyl group; Ry is a hydroxy group; and Rz is a hydrogen atom.

Compound (III-ii): a compound wherein Rx is a linear $C_{2-4}$ alkyl group substituted with at least one group selected from the group consisting of a $C_{1-6}$ alkyl group, a hydroxy group, an oxo group and a carboxyl group; and Ry and Rz form an oxo group.

More preferred examples of the compound (III) are as follows.

Compound (III-a): a compound wherein Rx is a butyl group substituted with a hydroxy group and a phosphoric group; Ry is a hydroxy group; and Rz is a hydrogen atom; for example, 6-phospho-D-gluconic acid.

Compound (III-b): a compound wherein Rx is an ethyl group substituted with a $C_{1-6}$ alkyl group; and Ry and Rz form an oxo group; for example, 3-methyl-2-oxobutanoic acid.

Compound (III-c): a compound wherein Rx is an ethyl group substituted with a carboxyl group; Ry is a hydroxy group; and Rz is a hydrogen atom; for example, 2-hydroxyglutaric acid.

In an aspect of the present invention, (A4) is particularly preferably a compound selected from 6-phospho-D-gluconic acid, 3-methyl-2-oxobutanoic acid and 2-hydroxyglutaric acid, or a salt thereof (which may be a hydrate).

In another aspect of the present invention, (A4) is particularly preferably 6-phospho-D-gluconic acid, or a salt thereof (which may be a hydrate).

A compound (A5) is at least one compound selected from the group consisting of creatinine, hydroxyproline, 1,3-butanediol, trientine, D-cellobiose, 1,3-dimethylurea and pantolactone and trimethadione, or a salt thereof. The compound (A5) may be a hydrate.

In an aspect of the present invention, (A5) is particularly preferably a compound selected from creatinine, hydroxyproline, 1,3-butanediol, 1,3-dimethylurea, pantolactone and trimethadione, or a salt thereof (which may be a hydrate).

As a salt included in each of the definitions of compounds (A1) to (A5), a pharmacologically acceptable salt is preferable. Examples of the salt include a salt with an inorganic base, a salt with an organic base, a salt with an inorganic acid, a salt with an organic acid and a salt with a basic or acidic amino acid.

Preferred examples of the salt with an inorganic base include an alkali metal salt such as a sodium salt and a potassium salt; an alkaline earth metal salt such as a calcium salt and a magnesium salt; an aluminum salt; and an ammonium salt. Preferably, a sodium salt, a potassium salt, a calcium salt and a magnesium salt are mentioned; and more preferably, a sodium salt, a potassium salt and a magnesium salt are mentioned.

Preferred examples of the salt with an organic base include salt with trimethylamine, triethylamine, pyridine, picoline, ethanolamine, diethanolamine, triethanolamine, tromethamine [tris(hydroxymethyl)methylamine], tert-butylamine, cyclohexylamine, benzylamine, dicyclohexylamine and N,N-dibenzylethylenediamine.

Preferred examples of the salt with an inorganic acid include salts with hydrofluoric acid, hydrochloric acid, hydrogen bromide, hydrogen iodide, nitric acid, sulfuric acid and phosphoric acid. Preferably, a salt with hydrochloric acid and a salt with phosphoric acid are mentioned.

Preferred examples of the salt with an organic acid include salts with formic acid, acetic acid, trifluoro acetic acid, phthalic acid, fumaric acid, oxalic acid, tartaric acid, maleic acid, citric acid, succinic acid, malic acid, methanesulfonic acid, benzene sulfonic acid and p-toluenesulfonic acid.

Preferred examples of the salt with a basic amino acid include salts with arginine, lysine and ornithine.

Preferred examples of the salt with an acidic amino acid include salts with aspartic acid and glutamic acid.

The (B) salt is a compound to be contained in the solution for transduction of the present invention independently from the salts included in each definitions of (A1) to (A5). In the present invention, the salts corresponding to those included in definitions of the compounds (A1) to (A5) are excluded from examples of the (B) salt.

Examples of the (B) salt include an alkali metal salt and an alkaline earth metal salt such as a lithium salt, a sodium salt, a magnesium salt, a potassium salt, a calcium salt, a rubidium salt and a cesium salt; an inorganic acid salt such as a carbonate, a sulfonate and a sulfate; an organic acid salt such as aspartate; a sulfide; and a halide such as a chloride, a bromide, an iodide and a fluoride. Of the (B) salts, an alkali metal salt, an alkaline earth metal salt, an organic acid salt and a chloride are preferable; more specifically, salts formed of an alkali metal or an alkaline earth metal (cation) and an organic acid or a halogen atom (anion), such as sodium chloride, magnesium chloride, potassium chloride and magnesium aspartate, are more preferable. These salts are preferably used in combination as the (B) salt. Examples of the combination of the salts serving as the (B) salt, which are not particularly limited, preferably include a combination of three salts: sodium chloride, magnesium chloride and potassium chloride. If the combination of three salts: sodium chloride, magnesium chloride and potassium chloride are used, the molar ratios of sodium chloride, magnesium chloride and potassium chloride are preferably 0.75 to 0.95, 0.05 to 0.15, and 0.025 to 0.075, respectively.

The types (combination) and concentrations of compounds to be used as components (A1) to (A5) and (B) in the solution for transduction of the present invention can be appropriately controlled depending on, for example, the type of target cell in consideration of introduction efficiency of a molecule(s) of interest into the cell, and are not particularly limited.

The concentrations of compounds (A1) to (A5) in the solution for transduction usually fall within the range of 0.1 mM to 1000 mM; however, optimal concentrations of them varies depending on the substance to be transduced. In the case of 2'-deoxycytidine, a concentration of 12.5 mM or more is preferable and a concentration of 100 mM to 250 mM is more preferable. In the case of calcium pantothenate, a concentration of 160 mM to 250 mM is preferable. In the case of disodium argininosuccinate hydrate, a concentration of 30 mM or more is preferable and a concentration of 100 mM to 250 mM is more preferable. In the case of sodium 3-methyl-2-oxobutyrate, a concentration of 40 mM or more is preferable and a concentration of 100 mM to 200 mM is more preferable. In the case of 1,3-butylene glycol, a concentration of 0.6 mM or more is preferable and a concentration of 0.6 mM to 3 mM is more preferable. In the case of 1,3-dimethylurea, a concentration of 30 mM or more is preferable and a concentration of 60 mM to 500 mM is more preferable. In the case of 2'-deoxyuridine, a concentration of 10 mM or more is preferable and a concentration of 100 mM or more is more preferable. In the case of 6-phospho-D-gluconic acid, a concentration of 60 mM or more is preferable and a concentration of 100 mM to 500 mM is more preferable. In the case of creatinine, a concentration of 5 mM or more is preferable and a concentration of 100 mM to 500 mM is more preferable. In the case of cytosine, a concentration of 20 mM or more is preferable and a concentration of 25 mM to 250 mM is more preferable. In the case of D (+)-cellobiose, a concentration of 3 mM or more is preferable and a concentration of 200 mM to 500 mM is more preferable. In the case of 2-deoxy-D-glucose-6-phosphate, a concentration of 30 mM or more is preferable and a concentration of 125 mM to 500 mM is more preferable. In the case of α-D-glucose-1-phosphate, a concentration of 60 mM or more is preferable and a concentration of 125 mM to 500 mM is more preferable. In the case of N-carbamyl-L-aspartic acid, a concentration of 60 mM or more preferable and a concentration of 125 mM to 500 mM is more is preferable. In the case of L-carnosine, a concentration of 1 mM or more is preferable and a concentration of 60 mM to 500 mM is more preferable. In the case of miglitol, a concentration of 1 mM or more is preferable and a concentration of 60 mM to 250 mM is more preferable. In the case of inosine 5'-disodium phosphate hydrate, a concentration of 100 mM or more is preferable and a concentration of 250 mM to 500 mM is more preferable. In the case of 2-hydroxyglutaric acid, a concentration of 1 mM or more is preferable and a concentration of 60 mM to 500 mM is more preferable. In the case of 1-methyl-L-histidine, a concentration of 10 mM or more is preferable and a concentration of 100 mM to 250 mM is more preferable. In the case of cytidine, a concentration of 100 mM or more is preferable and a concentration of 125 mM to 500 mM is more preferable. In the case of 6-phospho-D-gluconic acid, a concentration of 30 mM or more is preferable and a concentration of 100 mM to 250 mM is more preferable.

As to the concentration of the (B) salt in the solution for transduction, the concentration of a single type of salt or a total concentration of salts if two types or more of salts are used in combination usually falls within the range of 200 mM or more, preferably 200 to 2000 mM, and more preferably 300 mM to 900 mM.

Compounds (A1) to (A5), and the (B) salt can be produced (e.g., synthesized, isolated, purified) by methods known in the technical field or commercially available products of these can be used.

The solution for transduction of the present invention can be prepared by dissolving, at least one selected from compounds (A1) to (A5), and the (B) salt in an appropriate solvent.

The solvent for dissolving components (A1) to (A5) and (B) is not particularly limited as long as it can dissolve these components in a predetermined amount; however a buffer solution (buffer) is preferable. Examples of the buffer solution include an acid buffer solution such as an acetate buffer solution, a citrate buffer solution, a 2-morpholineethanesulfonic acid (MES) buffer solution and a phosphate buffer solution; and a neutral buffer solution such as a 4-(2-hydroxyethyl)-1-piperazineethanesulfonic acid (HEPES) buffer solution, a tris(hydroxymethyl)aminomethane (Tris) buffer solution, a phosphate buffer solution and a phosphate buffered saline (PBS).

The osmotic pressure of the solution for transduction of the present invention is not particularly limited; however, the osmotic pressure is usually 300 mOsmol/kg or more, preferably 300 to 2000 mOsmol/kg and more preferably 700 to 1700 mOsmol/kg.

Note that, in the present invention, the function effect of the present invention can be exerted and a molecule(s) of interest can be introduced into a cell with a high efficiency without using a transmembrane carrier, which is selected from viral plasmids, nanoparticles, liposomes, cationic lipids, outer membrane vesicles or other lipid vesicles (including micelles) and cell membrane permeability peptide and used in conventional transduction (transfection) methods known in the technical field.

Now, the transduction method of the present invention will be described.

The transduction method of the present invention at least comprises a step of contacting cells with a molecule(s) of interest and a solution for transduction (hereinafter referred to as a "contact step"), if necessary, other steps in connection with introduction of a molecule(s) of interest into a cell may be further included. The transduction method of the present invention uses a predetermined solution for transduction described herein for introducing a molecule(s) of interest into a cell; however, technical matters except the solution may follow those used in a method for transducing a molecule(s) of interest into a cell using a conventional solution.

Note that, in the present invention, the function effect of the present invention can be exerted and a molecule(s) of interest can be introduced into a cell with a high efficiency without employing a specific treatment such as electroporation used in transduction (transfection) methods known in the technical field.

Molecule(s) of Interest

In the present invention, the molecule(s) of interest to be introduced into a cell using a solution for transduction, is not particularly limited as long as the molecule(s) can exert a predetermined action in the cell. Examples of the molecule(s) of interest include a nucleic acid, a protein and a complex of these, and a high molecular compound (e.g., dextran). Preferred examples of the molecule (s) of interest include a nucleic acid, a protein and a complex of these.

The "nucleic acid" is not limited as long as it is a polymer of a nucleotide or a molecule having the same function as the nucleotide. Examples of the nucleic acid include RNA which is a ribonucleotide polymer, DNA which is a deoxyribonucleotide polymer, a polymer of a mixture of a ribonucleotide and a deoxyribonucleotide, and a nucleotide polymer containing a nucleotide analog. Furthermore, a nucleotide polymer containing a nucleic acid derivative may be used. The nucleic acid may be a single-stranded nucleic acid or a double-stranded nucleic acid. Examples of the double-stranded nucleic acid include a double-stranded nucleic acid, one strand of which hybridizes with the other strand in stringent conditions.

As the nucleotide analog, any molecule may be used as long as it is formed by modifying a ribonucleotide, a deoxyribonucleotide, RNA or DNA in order to improve resistance to a nuclease, stabilization, affinity for a complementary-strand nucleic acid and cell permeability in comparison with RNA or DNA, or in order to visualize the molecule. As the nucleotide analog, a naturally occurring molecule or a non-natural molecule may be mentioned. Examples thereof include a nucleotide analog having a modified sugar and a nucleotide analog having a modified phosphodiester bond.

The nucleotide analog having a modified sugar is not limited as long as it is formed by adding/substituting a chemical structure of a substance to/for a part or whole of the chemical structure of a sugar of a nucleotide. Examples of the nucleotide analog having a modified sugar include, a nucleotide analog substituted with 2'-O-methyl ribose; a nucleotide analog substituted with 2'-O-propyl ribose; a nucleotide analog substituted with 2'-methoxyethoxyribose, a nucleotide analog substituted with 2'-O-methoxyethyl ribose; a nucleotide analog substituted with 2'-O-[2-(guanidinium)ethyl] ribose, a nucleotide analog substituted with 2'-fluororibose, a nucleic acid analog (morpholino nucleic acid) the sugar moiety of which is substituted with a morpholino ring; a crosslinked artificial nucleic acid (bridged nucleic acid (BNA)) having two ring structures formed by introducing a crosslink structure into the sugar moiety, more specifically, such as a locked nucleic acid: (LNA) formed by crosslinking the 2'-position oxygen atom and the 4'-position carbon atom via methylene, an ethylene bridged nucleic acid (ENA) [Nucleic Acid Research, 32, e175 (2004)], an amido-bridged nucleic acid (AmnNA) obtained by crosslinking the 2'-position carbon atom and the 4'-position carbon atom via an amide bond, a peptide nucleic acid (PNA) [Acc. Chem. Res., 32, 624 (1999)]; an oxypeptide nucleic acid (OPNA) [J. Am. Chem. Soc., 123, 4653 (2001)]; and a peptide ribonucleic acid (PRNA) [J. Am. Chem. Soc., 122, 6900 (2000)].

The nucleotide analog having a modified phosphodiester bond is not limited as long as it is obtained by adding/substituting a chemical structure of a substance to/for a part or whole of the chemical structure of a phosphodiester bond of a nucleotide. Examples of the nucleotide analog having a modified phosphodiester bond include a nucleotide analog substituted with a phosphorothioate bond; and a nucleotide analog substituted with N3'-P5' phosphoamidate bond [Cell engineering, 16, 1463-1473 (1997)][RNAi method and antisense method, Kodansha Ltd. (2005)].

As the nucleic acid derivative, any molecule may be used as long as it is modified by adding, to a nucleic acid, a chemical substance in order to improve resistance to a nuclease, stabilization, affinity for a complementary-strand nucleic acid and cell permeability in comparison with the nucleic acid or in order to visualize the molecule. Examples of the nucleic acid derivative include a 5'-polyamine-added derivative, a cholesterol-added derivative, a steroid-added derivative, a bile acid added derivative, a vitamin-added derivative, a Cy5 added derivative, a Cy3-added derivative, a 6-FAM added derivative and a biotin-added derivative.

Examples of the nucleic acid include mRNA, siRNA, shRNA, miRNA, miRNA mimic, antisense nucleic acid, ribozyme, decoy nucleic acid, aptamer, plasmid DNA, Cosmid DNA, BAC DNA and guide RNA (gRNA) in the CRISPR system. These nucleic acids may be analogs having artificial modifications or derivatives thereof.

Examples of the protein include an enzyme, a transcription factor, a cytokine, a tissue growth factor, an antibody and a therapeutic protein. Examples of the enzyme include an enzyme targeting a nucleic acid (particularly genomic DNA in a target cell) and modifying the base sequence of the nucleic acid, such as a restriction enzyme, an endonuclease, Cre recombinase and flippase. Examples of the endonuclease include TAL effector nuclease (TALEN), zinc finger nuclease (ZFN), meganuclease (homing nuclease), a guide molecule (RNA) inducible endonuclease (e.g., Cas9, Cas12a) and other endonuclease for use in genome editing systems.

Preferred examples of a molecule(s) of interest in the present invention include substances for inducing gene modification in a target locus in a cell, in short, substances for use in genome editing, in particular, a substance for inducing genetic modification by the CRISPR system. Specifically, in a preferred embodiment of the present invention, the nucleic acid is guide RNA (gRNA) in the CRISPR system and the protein is an RNA guided nuclease in the CRISPR system. In a preferred embodiment of the present invention, a molecule(s) of interest is a complex of gRNA and an RNA guided nuclease such as Cas9 in the CRISPR system.

The details of the CRISPR system are known in the technical field and various applications are already known. Those skilled in the art can design, select and produce appropriate nucleic acids, proteins and other elements of the CRISPR system and carry out gene modification by the CRISPR system using them.

"Guide RNA" may be a single-strand RNA formed by ligating crRNA and tracrRNA, i.e., chimera RNA (sometimes also referred to as single guide RNA, sgRNA), or may have a form of discrete single RNAs (a combination of two or more RNA single strands). The guide RNA may have a form (one sgRNA or one set of crRNA and tracrRNA) targeting a single base sequence or a form (two or more sgRNAs or two or more sets of crRNA and tracrRNA) targeting two or more base sequences.

The crRNA contains a nucleic acid sequence consisting of about 17 to 20 bases (herein, sometimes referred to as a "target recognition sequence") hybridizing with a base sequence (herein, sometimes referred to as a "target sequence"), which is a target for gene modification in the genome or gene locus within a cell. The target sequence is located adjacent to a short sequence (called as a protospacer adjacent motif (PAM)) and recognized by the CRISPR system. The condition of the sequence and length of PAM vary depending on the type of nuclease to be employed; however, PAM is typically a sequence consisting of 2 to 5 base-pairs and located adjacent to a target sequence.

The target sequence is not particularly limited as long as it satisfies the above conditions for PAM and can be appropriately selected depending on the intended use. The target sequence is typically a sequence involved in a genetic disease, that is, a sequence contained in a gene locus, which is a potential target for gene therapy or contained in a gene locus involved in infection with a pathogen such as a bacterium and a virus.

In a preferred embodiment of the present invention, the target sequence is a base sequence of a gene locus containing a dystrophin gene. More specifically, the target sequence is a base sequence, a modification (deletion or insertion) of which corrects a frameshift mutation or a nonsense mutation of a dystrophin gene, thereby preventing or treating a dystrophinopathy (for example, muscular dystrophy such as Duchenne muscular dystrophy, Becker muscular dystrophy and dystrophin gene dilated cardiomyopathy). Alternatively, the target sequence is a base sequence of the dystrophin gene, which can produce dystrophin protein produced by gene correction of a frameshift mutation or a nonsense mutation.

Dystrophinopathy refers to various diseases caused by a dysfunctional dystrophin protein or dystrophin protein having an abnormal function caused by a mutation of the dystrophin gene. Examples of dystrophinopathy includes Duchenne muscular dystrophy, Becker muscular dystrophy and dystrophin gene-related dilated cardiomyopathy. In most cases, skeletal muscle disorder is a main symptom; however, there is a case where no skeletal muscle symptom is observed. Dystrophinopathy is sometimes associated with hypercreatininemia, myoglobinuria, dilated cardiomyopathy, cognitive impairment and the like.

Muscular dystrophy is defined as a "hereditary disease having degeneration and necrosis of skeletal muscle, as a main lesion, and progressive muscle weakness, as a clinical observation". Examples of the muscular dystrophy that is known include Duchenne muscular dystrophy, Becker muscular dystrophy, Emery-Dreifuss muscular dystrophy, limb-girdle muscular dystrophy, congenital muscular dystrophy, Miyoshi muscular dystrophy, distal muscular dystrophy, facioscapulohumeral muscular dystrophy and myotonic dystrophy.

Duchenne muscular dystrophy is pediatric muscular dystrophy known to have the largest number of patients and a prevalence rate of 4 to 5 per 100,000 persons. Progressive muscle atrophy is a main symptom and a dysfunctional by mutation dystrophin gene on the X chromosome is a cause. Over half patients with Duchenne muscular dystrophy has a single or a plurality of defective exons. The dystrophin-protein reading frame shifts by a dystrophin gene mutation and a stop codon appears in the middle of the frame, with the result that no dystrophin protein is synthesized, causing a series of symptoms.

The dystrophin gene is an extremely large gene consisting of more than 2,200,000 bases and present on X chromosome. Various isoforms are present due to different transcriptional initiation points. Examples of the isoforms that are known include Dp71 expressed in a whole body, Dp116 expressed in terminal nerve cells, Dp140 expressed in the brain and kidney, Dp260 expressed in the retina, Dp417p expressed in Purkinje neurons, Dp427b expressed in the brain, and Dp427m expressed in the skeletal muscle. Of them, dystrophin protein produced by Dp427m isoform is a protein expressed mainly in muscle cells. Dystrophin protein binds to cytoskeleton actin through the actin binding domain present at the N-terminal side and binds to a dystroglycan complex through the high-cysteine domain present at the C-terminal side to constitute the cytoskeleton in concert with actin. The dystrophin gene of Dp427m isoform is constituted of 79 exons.

In the case of patients with Duchenne muscular dystrophy, functional dystrophin protein is virtually not expressed (the amount of the protein detected by western blotting is 3% or less of that of a healthy person) due to a defective exon or duplicate mutation in the dystrophin gene or a point mutation (nonsense mutation) of a base in an exon or insertion/defective mutation (frameshift mutation). Whereas, in the case of patients with Becker muscular dystrophy, which is relatively milder than Duchenne muscular dystrophy, even if a defective exon and a base point-mutation are present, if a stop codon is not present in the middle, dystrophin protein having a shorter amino acid sequence than normal dystrophin protein or a partial amino acid substitution, is expressed.

As the mutation of the dystrophin gene in Duchenne muscular dystrophy and Becker muscular dystrophy, deletion of a single or a plurality of exons occupies a half or more of the mutation. Particularly, the site where a lot of deletions are found is known to be present between exon 44 and exon 55. Depending on the site of defective exon in a dystrophin gene, and for example, by referring to previously reported papers (e.g., van Deutekom J C, van Ommen G J., Nat Rev Genet. 2003), if can be confirmed which exon(s) should be skipped in order to express a repaired dystrophin. As a method for expressing dystrophin by correcting a gene mutation by genome editing other than exon skipping, a method of adjusting a reading frame by introducing a minor defect or insertion in the dystrophin gene and a method of inserting a missing exon by homologous recombination are mentioned.

If there is an abnormality as mentioned above in a dystrophin gene, the abnormality can be corrected by any one of the following operations: (i) skipping one or two or more exons so as not to be integrated into mRNA and joining exons sandwiching the skipped site to prevent a frameshift, (ii) inserting or deleting one or two or more bases to correct a frameshift and (iii) knocking-in a missing exon. If the above (i) or (ii) is selected, dystrophin protein having a shorter or longer amino acid sequence than that of a normal dystrophin protein or having a partial amino acid substitution is produced. If the above operation (ii) or (iii) is selected, normal dystrophin protein can be produced. Owing to such correction of a dystrophin gene, a disease such as muscular dystrophy can be prevented or treated.

The nucleotide sequence of a human dystrophin gene is available from, for example, the National Center for Biotechnology Information (ncbi.nlm.nih.gov/gene/1756).

The repaired dystrophin protein refers to dystrophin protein the expression of which is restored as a result of genome editing; in particular, refers to dystrophin protein having a N-terminal actin binding domain and a C-terminal high-cysteine domain, the expression of which is restored by applying genome editing to a dystrophin gene having a frameshift mutation or a nonsense mutation. In the case where a frameshift mutation occurs due to duplication of exons, if one of the two exons is skipped by genome editing, the expression of the repaired dystrophin protein having 100%-homology to a normal dystrophin protein may be sometimes restored. The repaired dystrophin protein particularly refers to human dystrophin protein translated from mRNA that is obtained by skipping exon 45 from a human dystrophin gene having a deletion of exon 44 and joining exon 43 and exon 46. Other than this, examples of the repaired dystrophin protein include, but are not limited to, dystrophin proteins produced by skipping a predetermined exon(s) in a human dystrophin gene having a deletion of, for example, exons 12-44, 18-44, 46-47, 46-48, 46-49, 46-51, 46-53, or 46-55. Whether repaired dystrophin protein is produced or not can be confirmed by detecting mRNA encoding repaired dystrophin protein contained in a cell by PCR, or by determining the molecular weight of the dystrophin protein based on western blotting using an antibody recognizing dystrophin protein.

In another preferred embodiment of the present invention, a target sequence is a base sequence of a locus containing a myostatin gene. More specifically, the target sequence is a base sequence whose modification (deletion or insertion) induces a frameshift mutation or a nonsense mutation of the myostatin gene, with the result that the function of the myostatin protein is terminated or reduced, inducing muscle hypertrophy.

In an embodiment of the present invention, it is preferable that at least a part of guide RNA consists of a nucleotide analog as described herein. As the nucleotide analog, a sugar-modified nucleotide and a phosphodiester bond modified nucleotide are preferable, and more specifically, a nucleotide analog having 2'-O-methyl ribose and a nucleotide analog formed by substituting the phosphodiester bond with a phosphorothioate bond. In guide RNA, it is preferable that at least a single base of each of the 3' and 5' ends of the sequence is a nucleotide analog, and more preferable that at least two bases or three bases at each of the 3' and 5' ends of the sequence are nucleotide analogs.

If the guide RNA is chimera RNA consisting of crRNA and tracrRNA, it is preferable that at least a single base of each of the 3' and 5' ends of the sequence is a nucleotide analog. If the guide RNA consists of discrete single strands of crRNA and tracrRNA (a combination of two RNA single strands) or has a form of more than two RNA strands, to each of which neither crRNA nor tracrRNA is connected, it is preferable that at least a single base of each of the 3' and 5' ends of each sequence of the RNA strands is a nucleotide analog (for example, both 3' and 5' ends of crRNA and both 3' and 5' ends of tracrRNA are preferably nucleotide analogs).

An "RNA guided endonuclease" is a protein containing at least one nuclease domain and at least one domain interacting with gRNA, and forming a complex with gRNA, thereby being guided to a target site.

The RNA guided endonuclease can be derived from the CRISPR system. The CRISPR system may be type I, type III, type IV of class 1 or type II, type V, and type VI system of class 2. Non-limiting examples of the appropriate CRISPR/Cas protein include Cas3, Cas4, Cas5, Cas5e (or, CasD), Cas6, Cas6e, Cas6f, Cas7, Cas8a1, Cas8a2, Cas8b, Cas8c, Cas9, Cas10, Cas10d, Cas12a (or Cpf1), Cas12b (or C2c1), Cas12c, Cas13a1 (or C2c2), Cas13a2, Cas13b, CasF, CasG, CasH, Csy1, Csy2, Csy3, Cse1 (or CasA), Cse2 (or CasB), Cse3 (or CasE), Cse4 (or CasC), Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csz1, Csx15, Csf1, Csf2, Csf3, Csf4 and Cu1966.

In an aspect, the RNA guided endonuclease is derived from the CRISPR system of class 2 type II. In a predetermined aspect, the RNA guided endonuclease is derived from Cas9 protein. Cas9 protein may be derived from, *Streptococcus pyogenes, Streptococcus thermophilus, Streptococcus*, sp., *Staphylococcus aureus, Staphylococcus* sp., *Nocardiopsis dassonvillei, Streptomyces pristinaespiralis, Streptomyces viridochromogenes, Streptosporangium roseum, Alicyclobacillus acidoterrestris, Bacillus pseudomycoides, Bacillus selenitireducens, Exiguobacterium sibiricum, Francisella novicida, Lactobacillus delbrueckii, Lactobacillus salivarius, Geobacillus stearothermophilus, Micorscillamarina, Burkholderia* sp., *Polaromonas naphthalenivorans, Polaromonas* species, *Crocosphaera watsonii, Cyanothece*, sp., *Microcystis aeruginosa, Synechococcus* sp., *Acetohalobium arabaticum, Ammonifex degensii, Caldicellulosiruptor becscii, Campylobacter jejuni, Campylobacter coli, Neisseria meningitides Candidatus Desulforudis, Clostridium botulinum, Clostridium difficile, Finegoldia magna, Natranaerobius thermophilusm, Propionibacterium thermopropionicum, Acidithiobacillus caldus, Acidithiobacillus ferrooxidans, Allochromatium vinosum, Marinobacter* sp., *Nitrosococcus halophilus, Nitrosococccus watsoni, Pseudoalteromonas haloplanktis, Ktedonobacter racemifer, Methanohalbium evestigatum, Anabaena variabilis, Nodularia spumigena, Nostoc* sp., *Arthrospira maxima, Arthrospira platensis, Arthrospira* sp., *Lyngbya* sp., *Microcoleus chthonoplastes, Oscillatoria*, sp., *Petrotoga mobilis, Thermosipho africanus* or *Caryochloris marina.*

In an aspect, RNA guided endonuclease is derived from Class 2, type V, CRISPR-Cas12a/Cpf1 system. In a predetermined aspect, RNA guided endonuclease is derived from Cpf1 protein. Cpf1 protein may be derived from *Acidaminococcus*, Lachnospiraceae, *Chlamydomonas reinhardtii*, or *Francisella novicida.*

CRISPR/Cas protein may be a wild-type CRISPR/Cas protein, a modified CRISPR/Cas protein or a fragment of the wild-type or modified CRISPR/Cas protein. CRISPR/Cas protein may be modified in order to increase binding affinity and/or specificity to a nucleic acid, change enzyme activity, or change another characteristic of the protein.

RNA guided nuclease may be Cas nuclease or Cas nickase. The Cas nuclease or Cas nickase herein refers to an essential protein component in the CRISPR/Cas system and means an endonuclease or a nickase exerting an activity when it forms a complex with two types of RNAs called CRISPR RNA (crRNA) and transactivated crRNA (tracrRNA). The nickase refers to a DNA cleavage enzyme producing a nick only one of DNA strands. Generally, the Cas9 protein contains at least two nuclease (i.e., DNase) domains For example, the Cas9 protein contains RuvC-like nuclease domain and HNH-like nuclease domain. RuvC and HNH domains work together to produce a single strand break in order to produce double-stranded breaks in DNA (Jinek et al., Science, 337: 816-821). In an aspect, a Cas9-derived protein may be modified so as to contain only one functional nuclease domain (RuvC-like or HNH-like nuclease domain). For example, a Cas9-derived to protein may be modified by deletion or mutation such that one of the nuclease domains is no longer functional (i.e., nuclease activity is not present). In an aspect where one of the nuclease domains is inactive, the Cas9-derived protein can produce a nick in a double-stranded nucleic acid; however, the protein cannot cut the double-stranded nucleic acid (DNA). For example, in the RuvC-like domain, if aspartic acid is changed to alanine (D10A), a Cas9-derived protein is changed to a nickase. Similarly, in the HNH domain, if histidine is changed to alanine (H840A or H839A), a Cas9-derived protein is changed to a nickase. Each of the nuclease domains may be modified by site-specific mutagenesis, PCR mediated mutagenesis, whole gene synthesis and another method known in the technical field.

As the RNA guided nuclease, a Cas nuclease or a Cas nickase derived particularly from *Streptococcus* sp., *Staphylococcus* sp. *Francisella novicida* or *Campylobacter jejuni* may be used. Particularly, as the source from which Cas nuclease or Cas nickase is derived, *S. pyogenes* in the *Streptococcus* sp. and *S. aureus* in the *Staphylococcus* sp. are preferred. Cas9 nuclease or Cas9 nickase derived from *S. pyogenes* recognizes NGG or NAG trinucleotide as the PAM sequence.

As the RNA guided nuclease, Cas9 is preferable. In a preferred embodiment of the present invention, Cas9 refers to SpCas9S derived from *S. pyogenes* (*Streptococcus* sp.). As Cas 9, those derived from various types of bacteria or archaea are known. Other than SpCas9, Cas 9 having a desired nuclease activity such as Cas9 (SaCas9) derived from *S. aureus*, can be used in the present invention.

In the transduction method of the present invention, the use amount of a molecule(s) of interest varies depending on the transduction conditions and the purpose thereof and can be appropriately adjusted by those skilled in the art. For example, if the molecule(s) of interest is gRNA, the use amount is usually 10 ng to 510 ng and preferably 16 ng to 255 ng for $1\times10^4$ cells. If the molecule(s) of interest is Cas9 protein, the use amount is usually 60 ng to 3200 ng and preferably 100 ng to 1600 ng.

Cell

A desired cell to which a molecule(s) of interest is to be introduced by use of the solution for transduction of the present invention is not particularly limited, and appropriately selected depending on the purpose. Examples of the target cell include a mesenchymal stem cell, a neural stem cell, a skin stem cell, a spleen cell, a nerve cell, a glial cell, a pancreas B cell, a bone marrow cell, a mesangial cell, a Langerhans cell, an epidermal cell, an epithelial cell, an endothelial cell, a fibroblast, a fiber cell, a muscle cell (e.g., a skeletal muscle cell, a cardiomyocyte, a myoblast, a muscle satellite cell, a smooth muscle cell), a fat cell, a blood cell (e.g., a macrophage, a T cell, a B cell, a natural killer cell, a mast cell, a white blood cell, a neutrophil, a basophil, an eosinophil, a monocyte, a megakaryocyte, a hematopoietic stem cell), a synovial cell, a chondrocyte, a bone cell, an osteoblast, an osteoclast, a mammary gland cell, a hepatocyte, a stromal cell, an egg cell and a sperm cell, and a progenitor cell that can be differentiated into these cells, a stem cell (including, for example, an induced pluripotent stem cell (iPS cell), an embryonic stem cell (ES cell)), a primordial germ cell, an oocyte and a fertilized egg. These cells may develop into cancers cells.

The tissue or organ from which a target cell is derived when the transduction method of the present invention is carried out in vitro (ex vivo) or in culture (in vitro), or the tissue or organ in which a target cell is present when the transduction method of the present invention is carried out in vivo, is not particularly limited as long as the tissue or organ contains the target cell. Examples of the tissue or organ containing the target cell include, brain, sites of the brain (e.g., olfactory bulb, cranial nucleus, basal ganglia, hippocampus, thalamus, hypothalamus, subthalamic nucleus, cerebral cortex, medulla oblongata, cerebellum, occipital lobe, frontal lobe, temporal lobe, putamen, caudate nucleus, corpus callosum, substantia nigra), spinal cord, pituitary, stomach, pancreas, kidney, liver, gonad, thyroid, gall bladder, bone marrow, adrenal glands, skin, lung, gastrointestinal tract (e.g., colon, small intestine), blood vessel, heart, thymus, spleen, submandibular gland, peripheral blood, peripheral blood cells, prostate, placenta, uterus, bone, joint and muscle (e.g., skeletal muscle, smooth muscle, myocardium). In a preferred embodiment of the present invention, the tissue or organ containing a target cell is the muscle, brain and a site of the brain. In a more preferred embodiment of the present invention, the tissue or organ containing a target cell is muscle. These tissues or organs may develop into cancer tissues or organs (cancer tissue, etc.).

The target cell may be a human-derived cell or a cell derived from a mammal except a human (non-human mammal). Examples of a non-human mammal include a mouse, a rat, a hamster, a guinea pig, a rabbit, a dog, a cat, a pig, a cow, a horse, a sheep and a primate except a human (non-human primate such as cynomolgus monkey, rhesus monkey, chimpanzee).

In a preferred embodiment of the present invention, the target cell is a muscle cell (e.g., a cardiomyocyte, a skeletal muscle cell, a muscle satellite cell), a neural stem cell, a nerve cell, a glial cell, a fibroblast, a mesenchymal stem cell, a blood cell or an iPS cell. In a more preferred embodiment of the present invention, the target cell is a muscle cell, in particular, a skeletal muscle cell or a satellite cell. Examples of the muscle cell include muscle cells taken from a human (patient or healthy person), a mammal except a human (for example, a disease-model animal such as a non-human primate (e.g., cynomolgus monkey, rhesus monkey, chimpanzee), a cow, a pig, a mouse and a rat); and muscle cells differentiated from muscle cells present in a living body (e.g., in tissues of a human of a living body), a muscle cell line and stem cells (e.g., iPS cells, ES cells).

Step of Contacting Cells with Molecule of Interest and Solution for Transduction In the transduction method of the present invention, a manner of contacting cells with a molecule(s) of interest and a solution for transduction is not particularly limited. Any manner can be selected as long as it can introduce a molecule(s) of interest into a cell at a desired efficiency.

When the transduction method of the present invention is carried out ex vivo or in culture (in vitro), a molecule(s) of interest and a solution for transduction are added to a culture medium (if necessary, in a form of solution in which they are previously mixed therein) and a target cell is cultured in the culture medium. In this manner, the molecule(s) of interest and solution for transduction can be contacted with the cell.

As the culture medium, a medium known in the technical field and appropriate for culturing a cell population including a target cell can be used. Examples of the culture medium that can be used include BME medium, BGJb medium, CMRL 1066 medium, Glasgow MEM medium, improved MEM (IMEM) medium, improved MDM (IMDM) medium, Medium 199 medium, Eagle MEM medium, αMEM medium, DMEM medium (high glucose, low glucose), DMEM/F12 medium, Ham medium, RPMI 1640 medium, Fischer's medium, StemFit AK02N, primate ES cell medium and a mixed medium of these. The type and use amount of the culture medium can be appropriately set by those skilled in the art depending on the type of cell and culture conditions.

To a culture medium, if necessary, additives such as an essential or non-essential amino acid, GlutaMAX (product name), a vitamin, an antibiotic substance (for example, penicillin, streptomycin, or a mixture of these), an antibacterial agent (for example, amphotericin B), an antioxidant, a pyruvic acid, a buffer and an inorganic salt may be added. The types and use amounts of additives can be appropriately set by those skilled in the art depending on the type of cell and culture conditions.

In the case of contacting a cell with a molecule(s) of interest and a solution for transduction under a culture condition (in vitro), the time (period) of the step is not particularly limited as long as introduction can be achieved at a desired efficiency. The time (period) is usually 10 minutes to 180 minutes, and preferably 15 minutes to 60 minutes. The culture conditions except the time (period), such as a temperature and an atmosphere (carbon dioxide concentration), can be appropriately controlled by those skilled in the art.

When the transduction method of the present invention is carried out in vivo, a molecule(s) of interest and a solution for transduction can be contacted with a target cell by mixing the molecule(s) of interest with the solution for transduction to prepare an injection, such as an intravenous injection, an intraarterial injection, an intramuscular injection, a subcutaneous injection and an intraperitoneal injection, and administering the injection to a living body. The solution for transduction to be used in such an embodiment may contain, in addition to components (A1) to (A5) and (B), pharmaceutically acceptable additives for injection such as saline, buffered saline, water for injection, a stabilizer, a solubilizer, a surfactant, a buffer, a preservative, a tonicity agent, a filler, a lubricant and a thickener.

In a preferred embodiment of the present invention, a transduction method is used for modifying a dystrophin gene in muscle cells by the CRISPR system, in other words, for producing cells having a dystrophin gene modified by the CRISPR system or for producing dystrophin protein by modifying a dystrophin gene.

Now, a method for producing cells of the present invention will be described.

The method for producing cells of the present invention comprises a step of contacting at least cells with a molecule(s) of interest and the solution for transduction (contact step), and if necessary further comprises a step involved in production of cells having a molecule(s) of interest transduced therein. The method for producing cells according to the present invention employs a predetermined solution for transduction for introducing a molecule(s) of interest within a cell as described herein. Technical matters except the predetermined solution for transduction may be the same as those according to a method for producing cells having a molecule(s) of interest introduced therein by use of a conventional solution.

The contact step included in the method for producing cells according to the present invention is the same as the contact step described herein in connection with the transduction method of the present invention.

Examples of the step involved in production of cells having a molecule(s) of interest transduced therein, which may be further comprised, if necessary, in the method for producing cells according to the present invention, include (a) a step of selecting a cell having a molecule(s) of interest introduced therein, performed after the contact step, and (b) a step of differentiating target cells from pluripotent stem cells such as iPS cells or other stem cells, performed before the contact step.

In the above step (a), a cell having a molecule(s) of interest introduced therein can be selected by use of a known method. For example, in the case where a molecule(s) of interest is for use in the CRISPR system (typically, a complex of gRNA and Cas9 protein), a cell in which a molecule(s) of interest is introduced and a predetermined gene is modified can be selected by PCR and sequencing of the base sequence or by confirmation of an expressed protein by electrophoresis. Alternatively, a cell having a molecule (s) of interest introduced therein can be selected by introducing a drug resistance gene, a gene encoding a fluorescent protein, a positive selection marker gene or a negative selection marker gene into a cell together with the molecule(s) of interest, and applying a treatment corresponding to the gene introduced (for example, adding a drug corresponding to a drug resistance gene to a culture medium; irradiating light having the excitation wavelength corresponding to a fluorescent protein and detecting fluorescence emitted by irradiation, by a fluorescence microscope or a cell sorter; or adding an antibody recognizing a protein produced by a gene, fluorescently labeling the antibody bound to the protein and detecting fluorescence emitted by a fluorescence microscope or a cell sorter).

In the above step (b), differentiation induction from pluripotent stem cells such as iPS cells or other stem cells into target cells can be carried out by a known method. As an example of a differentiation induction method from pluripotent stem cells into target cells, a method reported by Laflamme M A et al., (Laflamme M A & Murry C E, Nature 2011; Review) is mentioned. Note that, if target cells can be obtained by such differentiation induction, a cell population containing the target cells may be an embryoid body.

Now, the pharmaceutical composition of the present invention will be described. Note that, those skilled in the art can be modify the present invention relating to "a pharmaceutical composition" into, for example, an invention relating to "therapeutic method" (for example, a method including a step of administering effective amounts of solution for transduction and a molecule(s) of interest to a human or non-human animal) based on the description of the specification and common technical knowledge.

The pharmaceutical composition of the present invention contains a solution for transduction and a molecule(s) of interest according to the present invention. The details of the "solution for transduction", "molecule(s) of interest" and preferable embodiments are the same as those separately described in the specification.

Application of the pharmaceutical composition of the present invention varies depending on the molecule(s) of interest to be contained therein. A pharmaceutical composition different in application can be prepared by selection of a molecule(s) of interest.

In a preferred embodiment of the present invention, a pharmaceutical composition is prophylactic or therapeutic drug for dystrophinopathy or a drug for producing a repaired dystrophin protein. In the embodiment, a molecule (s) of interest targets a base sequence of a locus containing a dystrophin gene and may be an element(s) to constitute the CRISPR system for modifying the base sequence, e.g., a complex of gRNA targeting a predetermined base sequence and Cas protein.

The dosage form of the pharmaceutical composition of the present invention is not particularly limited and can be appropriately selected based on the application. For example, as described in connection with the transduction method of the present invention, the pharmaceutical composition of the present invention can be prepared in the form of an injection such as an intravenous injection, an intraarterial injection, an intramuscular injection, a subcutaneous injection and an intraperitoneal injection.

The pharmaceutical composition of the present invention can further contain a substance such as a pharmaceutically acceptable additive other than a solution for transduction and a molecule(s) of interest, depending on the dosage form. The amount and concentration of an active ingredient (molecule(s) of interest) in the pharmaceutical composition of the present invention can be appropriately controlled in view of the dosage form, route of administration, dose per time and the number of doses during a predetermined period, in order that an effective amount of the active ingredient for the desired prevention or treatment of the effect can be delivered to a target cell.

EXAMPLES

In the following Examples, the compounds listed in the following tables were used.

TABLE 1-1

| No. | Classification | Compound name | Compound name | Catalog No. | Concentration of compound stock solution |
|---|---|---|---|---|---|
| (1.) | A1 | Disodium argininosuccinate hydrate<br>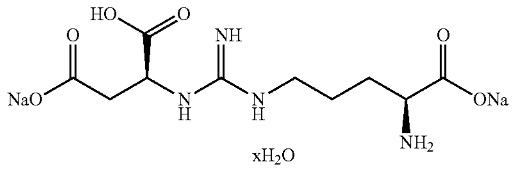 | Sigma-Aldrich | A5707 | 2000 mM |

TABLE 1-1-continued
| No. | Classi-fica-tion | Compound name | Compound name | Catalog No. | Concentration of compound stock solution |
|---|---|---|---|---|---|
| (2.) | A1 | 1-Methyl-L-hystidine<br>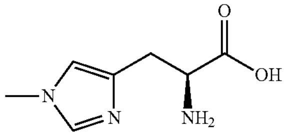 | Sigma-Aldrich | 67520 | 2000 mM or 500 mM |
| (3.) | A1 | Calcium pantothenate<br>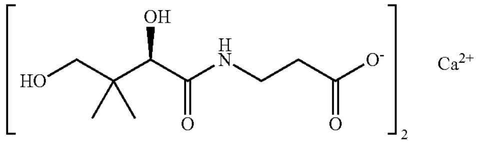 | Wako | 031-14161 | 2000 mM |
| (4.) | A1 | L-Camosine<br>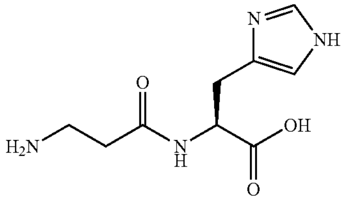 | Wako | 032-11031 | 1000 mM |
| (5.) | A1 | N-Carbamyl-L-aspartic acid<br>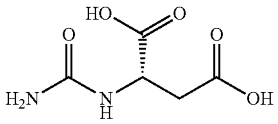 | Bachem AG | 40275370005 | 500 mM |
TABLE 1-2
| | | | | | |
|---|---|---|---|---|---|
| (6.) | A2 | Miglitol<br>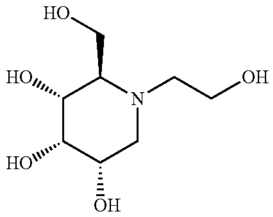 | Wako | 138-16221 | 500 mM |
| (7.) | A2 | 2-Deoxy-D-glucose-6-phosphate<br>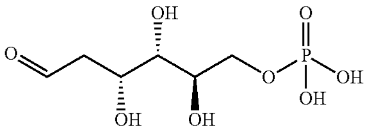 | CC | 17149 | 500 mM |

TABLE 1-2-continued
| | | | | | |
|---|---|---|---|---|---|
| (8.) | A2 | α-D-Glucose-1-phosphate | Wako | 194673 | 500 mM |
| | | 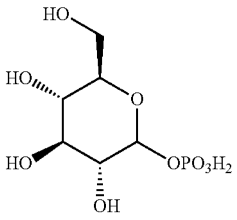 | | | |
| (9.) | A2 | 1-Deoxynojirimycin | Wako | 043-24931 | 500 mM |
| | | 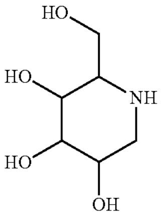 | | | |
| (10.) | A3 | Cytidine | Wako | 035-23231 | 500 mM |
| | | 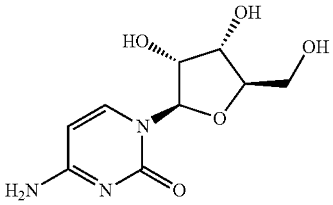 | | | |
TABLE 1-3
| | | | | | |
|---|---|---|---|---|---|
| (11.) | A3 | 2′-Deoxyuridine (deoxyuridine) | TCI | D0060 | 1000 mM |
| | | 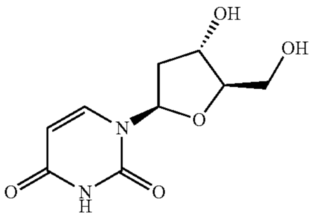 | | | |
| (12.) | A3 | 2′-Deoxycytidine (deoxycytidine) | Wako | QB-9843 | 2000 mM |
| | | 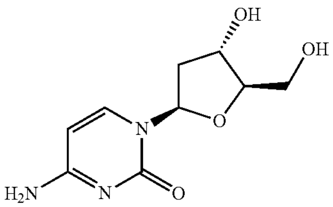 | | | |

TABLE 1-3-continued
| | | | | | |
|---|---|---|---|---|---|
| (13.) | A3 | Inosine 5′-disodium phosphate hydrate (5′-inosinic acid) 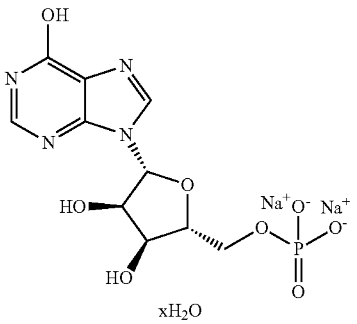 $xH_2O$ | TCI | I0036 | 800 mM |
| (14.) | A4 | 6-Phospho-D-gluconic acid 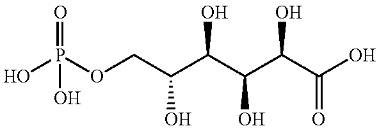 | Oriental Yeast | 45190000 | 1000 mM or 500 mM |
| (15.) | A4 | Sodium 3-methyl-2-oxobutate 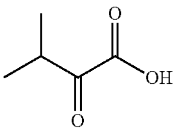 | Sigma-Aldrich | 198994 | 2000 mM |
TABLE 1-4
| | | | | | |
|---|---|---|---|---|---|
| (16.) | A4 | 2-Hydroxyglutaric acid 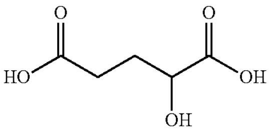 | TRC | H942575 | 2000 mM |
| (17.) | A5 | Creatinine 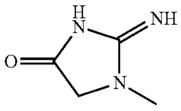 | Wako | 033-04591 | 500 mM |
| (18.) | A5 | 4-Hydroxyproline (hydroxyproline) 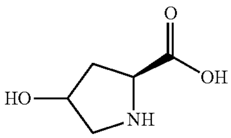 | Wako | 080-01642 | 1000 mM |

TABLE 1-4-continued

| | | | | | |
|---|---|---|---|---|---|
| (19.) | A5 | 1,3-Butylene glycol (1,3-butanediol)<br>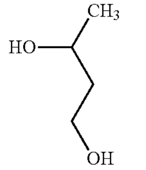 | Wako | 762J0 | 1000 mM |
| (20.) | A5 | Trientine hydrochloride<br>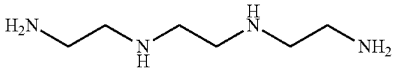<br>2HCl | Sigma-Aldrich | 90460-10 mL | 1000 mM |
| (21.) | A5 | D(+)(-)-Cellobiose (D-cellobiose)<br>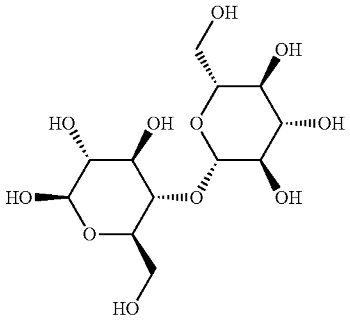 | Wako | 036-0741 | 1000 mM |

TABLE 1-5

| | | | | | |
|---|---|---|---|---|---|
| (22.) | A5 | 1,3-Dimethylurea<br>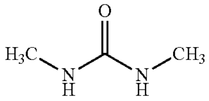 | Wako | 75LOX | 1000 mM |
| (23.) | A5 | (R)-Pantolactone (pantolactone)<br>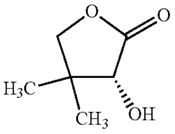 | TCI-JP | P0011 | 1000 mM |
| (24.) | A5 | Trimethadione<br>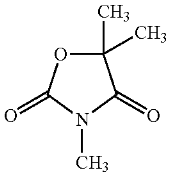 | Sigma-Aldrich | T0781-Sigma-1G | 1000 mM |

TABLE 1-5-continued

| | | | | | |
|---|---|---|---|---|---|
| (25.) | — | GABA (γ-aminobutyric acid) | Wako | 010-02441 | 2000 mM or 1000 mM |

Wako; FUJIFILM Wako Pure Chemical Corporation,
TCI-JP; Tokyo Chemical Industry Co., Ltd.,
TRC; Toronto research chemicals,
OY; Oriental Yeast Co., Ltd.,
CC; Cayman Chemical Company Materials BL21 (DE3) Competent *E. coli* (NEB, C2527)
Ni-NTA Superflow Cartridges (GE, 30765)
HiLoad 26/60 Superdex 200 pg (GE, 17-1071-01)
Resource S (GE, 17-1180-01)
TEV protease (Sigma, T4455)
Complete, EDTA free (Roche, 1873580)
SEM Nuclease, recombinant, solution (WAKO, 196-16181)
DTT (WAKO, 049-08972)
Imidazole (WAKO, 095-00015)
1 M Aqueous magnesium chloride solution (WAKO, 310-90361)
Magnesium aspartate (MP Biomedicals Inc., 150496)
10×TBS (Takarabio, T9141)
1 M HEPES buffer (Nacalai Tesque Inc., 17557-94)
0.5 M EDTA solution (Invitrogen, 15575-038)
LB medium (Lennox), (Sigma, L7275-500TAB)
2×YT culture medium, (Sigma, Y2627-1 kg)
IPTG (WAKO, 096-05143)
Ampicillin sodium (WAKO, 014-23302)
Potassium chloride (WAKO, 161-03541)

Pierce 660 nm protein assay (Thermo scientific, 22660)
D-MEM (High Glucose) with L-Glutamine and Phenol Red (WAKO, 044-29765)
0.25 w/v % Trypsin-1 mmol/1 EDTA-4Na Solution with Phenol Red (WAKO, 201-16945)
D-PBS (−), (WAKO, 043-29791)
5 M Sodium chloride, (Invitrogen, AM9759)
UltraPure DNase/RNase-Free Distilled Water (Invitrogen, 10977015)
Fetal Bovine Serum, qualified, USDA-approved regions (Gibco, 10437028)
CellCarrier Ultra PDL coated 96-well plate (PerkinElmer, 6055500)
HOECHST (registered trademark) 33342 (ThermoFisher, H3570)
C2C12 (ATCC (registered trademark), CRL-1772 (trademark))
Millex-GV 0.22 μm PVDF 4 mm EtO Ster sterilized (Merck, SLGV004SL)
3-(1-Pyridino)propane sulfonic acid (NDSB-201) (TCI-JP, S0813)
Glycerol (WAKO, 075-00616)
Glycine (WAKO, 070-05281)
Aqueous L-glutamine solution, X100 (WAKO, 073-05391)
NEAA, X100 (Life technologies, 11140-035)
N2 supplement, X100 (Gibco, 17502-048)
B27 Supplement (Gibco, 12587-010)
EGF (WAKO, 059-07873)
bFGF (WAKO, 064-05381)
Opti-MEM (trademark) I Reduced Serum Medium (Life technologies, 31985-062)
10×PBS-Phosphate-Buffered Saline (10×) pH 7.4; RNase-free (Invitrogen)
Amicon® Ultra 2 mL Centrifugal Filters 10 kDa (Merck)
Dextran, Alexa Fluor™ 488; 10,000 MW, Anionic, Fixable (Thermo Scientific)
4% paraformaldehyde phosphate buffer solution (WAKO)
ProLong™ Glass Antifade Mountant with NucBlue™ Stain (Thermo Scientific)

```
Base sequences of CrRNA and gRNA
MmDmdEx51 crRNA (GeneDesign, Inc):
                                              SEQ ID No. 1
5'-mC*mA*mC*UAGAGUAACAGUCUGACGUUUUAGAGCUAUGCUGUmU*

mU*mU*G-3'
(mN: 2'-O methyl RNA modification,
*: Phosphorothioate modification)

tracrRNA (GeneDesign, Inc):
                                              SEQ ID No. 2
5'-mC*mA*mA*AACAGCAUAGCAAGUUAAAAUAAGGCUAGUCCGUUAUC

AACUUGAAAAAGUGGCACCGAGUCGmG*mU*mG*C-3'
(mN: 2'-O methyl RNA modification,
*: Phosphorothioate modification)

MmDmd Ex51 gRNA#1 (mod):
                                              SEQ ID No. 3
5'-mU*mC*mA*CUAGAGUAACAGUCUGACGUUUUAGAGCUAGAAAUAGC

AAGUUAAAAUAAGGCUAGUCCGUUAUCAACUUGAAAAAGUGGCACCGAGU

CGGUGCmU*mU*mU*U-3'
(mN: 2'-O methyl RNA modification,
*: Phosphorothioate modification, GeneDesign, Inc)
```

-continued

```
mRosa26 gRNA (mod):
                                              SEQ ID No. 4
5'-mG*mA*mU*GGGCGGGAGUCUUCUGUUUUAGAGCUAGAAAUAGCAAG

UUAAAAUAAGGCUAGUCCGUUAUCAACUUGAAAAAGUGGCACCGAGUCGm

G*mU*mG*C-3'
(mN: 2'-O methyl RNA modification,
*: Phosphorothioate modification, GeneDesign, Inc,
or Sumitomokagaku, Inc.)

hEx45#1 gRNA (mod):
                                              SEQ ID No. 5
5'-mU*mG*mG*UAUCUUACAGGAACUCCGUUUUAGAGCUAGAAAUAGCA

AGUUAAAAUAAGGCUAGUCCGUUAUCAACUUGAAAAAGUGGCACCGAGUC

GmG*mU*mG*C-3'
(mN: 2'-O methyl RNA modification,
*: Phosphorothioate modification, GeneDesign, Inc)

hEx45#23 gRNA (mod):
                                              SEQ ID No. 6
5'-mA*mG*mC*UGUCAGACAGAAAAAAGGUUUUAGAGCUAGAAAUAGCA

AGUUAAAAUAAGGCUAGUCCGUUAUCAACUUGAAAAAGUGGCACCGAGUC

GmG*mU*mG*C-3'
(mN: 2'-O methyl RNA modification,
*: Phosphorothioate modification, GeneDesign, Inc)
```

<Equipment>

FACS Asia (trademark) (BD)
NEPA21 transfection system (NEPA GENE)
AKTAprime (GE)
Opera Phenix (trademark) High-Content Screening System (PerkinElmer)
Harmony (trademark) (PerkinElmer)

<Compounds>

Suppliers, catalog numbers of compounds and concentrations of compound stock solutions are collectively listed in Table 1.

<Description of Terms Used>

EGFP-SSA assay: an abbreviation of EGFP-single strand annealing assay. The reporter cassette shown in FIG. 1 is inserted in EGFP reporter cells. In the middle of the EGFP sequence of the cassette, MmDMD-Ex51 sequence is inserted. Since the presence of MmDMD-Ex51 sequence, by which EGFP ORF is divided, EGFP protein is not usually translated. However, when target sequence of MmDMD-Ex51 is cleaved by Cas9 protein/gRNA complex, the upstream region (EG part) and the downstream region (FP part) of EGFP ORF are annealed via a homology area into a single strand, with the result that a full-length EGFP ORF emerges to produce EGFP protein. Based on this principle, the ratio of the number of cells producing EGFP is checked by the EGFP-SSA assay. In this manner, the amount of Cas9 protein/gRNA complex delivered to cells can be predicted.

<Preparation of Reagent, Reaction Solution and Administration Solution>

Lysis Buffer

TBS (10×) (20 mL), 500 U/μL SEM nuclease (0.002 mL), 0.5 M EDTA solution (0.2 mL), 1 M aqueous magnesium chloride solution (0.2 mL), DTT (30.85 mg) and imidazole (272.308 mg) were added and dissolved in milliQ water and diluted up to 200 mL so as to obtain final concentrations: 1×TBS, 20 mM imidazole, 0.005 U/μL SEM nuclease, 1 mM DTT, 0.5 mM EDTA 2Na and 1 mM magnesium chloride. Six tablets of Complete EDTA free were add to the resultant solution, which was stirred and sterilized by with a filter having a pore size of 0.22 μm.

GF Buffer

A 1 M HEPES solution (20 mL), potassium chloride (11.182 g) and DTT (154.25 mg) were added and dissolved in milliQ water so as to obtain final concentrations: 20 mM HEPES, 150 mM potassium chloride and 1 mM DTT (pH 7.5). After the pH of the resultant solution was adjusted to be 7.5, the solution was diluted up to 1000 mL and sterilized by a filter having a pore size of 0.22 μm.

Culture Medium for C2C12 Cells (Mouse Striated Muscle Cells)

D-MEM (high glucose) medium with L-glutamine and phenol red containing 10% FBS (volume/volume)

Compound Stock Solution

Suppliers of compounds and the final concentrations of compounds in stock solutions are shown in Table 1. Individual compounds were weighed and dissolved with UltraPure DNase/RNase-Free Distilled Water so as to obtain the final concentrations shown in Table 1. The resultant solutions were sterilized by a 0.22 μm filter to obtain compound stock solutions.

Reaction Solution 1

Cas9 protein (0.4 μg), tracrRNA (34.18 ng), MmDmd Ex51 crRNA (29.48 ng), a 1 M HEPES buffer (0.05 μL) and a 5 M aqueous sodium chloride solution (5.5 μL) were mixed and diluted with UltraPure DNase/RNase-Free Distilled Water up to a liquid volume of 37.5 μL so as to obtain final concentrations: 8 ng/μL Cas9 protein, 0.68 ng/μL tracrRNA, 0.59 ng/μL MmDmd Ex51 crRNA, 1 mM HEPES, 550 mM sodium chloride, and 250 mM compound. To this solution, a 1000 mM compound solution (12.5 μL) was added and the solution mixture was incubated at normal temperature for 15 minutes. Note that, in the cases where the final concentrations of the compound are 0.1 mM, 0.15 mM, 0.34 mM, 0.69 mM, 1 mM, 1.38 mM, 5 mM, 6.38 mM, 10 mM, 20 mM, 40 mM, 60 mM, 80 mM, 100 mM, 125 mM, 200 mM and 500 mM, the compound stock solutions were diluted with UltraPure DNase/RNase-Free Distilled Water up to concentrations of 0.4 mM, 0.6 mM, 1.36 mM, 2.76 mM, 4 mM, 5.52 mM, 20 mM, 25.5 mM, 40 mM, 80 mM, 160 mM, 240 mM, 320 mM, 400 mM, 500 mM, 800 mM and 2000 mM, respectively, and then added.

Reaction Solution 2

Cas9 protein (0.4 μg), tracrRNA (34.18 ng), MmDmd Ex51 crRNA (29.48 ng), a 1 M HEPES buffer (2.5 μL) and a 5 M aqueous sodium chloride solution (4.85 μL) were mixed and diluted with UltraPure DNase/RNase-Free Distilled Water up to a liquid volume of 37.5 μL so as to obtain final concentrations: 8 ng/μL Cas9 protein, 0.68 ng/μL tracrRNA, 0.59 ng/μL MmDmd Ex51 crRNA, 50 mM HEPES, 485 mM sodium chloride, and 250 mM compound. To this solution, a 1000 mM compound solution (12.5 μL) was added and the solution mixture was incubated at normal temperature for 15 minutes. Note that, in the cases where the final concentrations of the compound are 0.69 mM, 25 mM, 100 mM, 125 mM, 160 mM, 200 mM and 500 mM, the compound stock solution was diluted with UltraPure DNase/RNase-Free Distilled Water up to concentrations of 2.76 mM, 100 mM, 400 mM, 500 mM, 640 mM, 800 mM and 2000 mM, respectively, and then, added.

iTOP-1250 Buffer

In accordance with Patent Literature 2, iTOP-1250 buffer was prepared. Individual reagents were added to an Opti-MEM-base solution so as to obtain final concentrations: 200 mM GABA, 50 mM NDSB-201, 15 mM glycine, 30 mM glycerol, 425 mM sodium chloride, 0.75× glutamine, 0.75× Non-Essential amino Acids, 0.75× N-2 supplement, 0.75× B-27 supplement, 100 ng/μL FGF2, 100 ng/μL EGF, 8 ng/μL Cas9 protein, 0.68 ng/μL tracrRNA and 0.59 ng/μL MmDmd Ex51 crRNA, and incubated at normal temperature for 15 minutes. Preparation was carried out with reference to Non Patent Literature 1. Opti-MEM is contained in iTOP-1250 buffer in a ratio of 60%.

Reaction Solution 3-1

Cas9 protein (2.0 μg), tracrRNA (170.9 ng), MmDmd Ex51 crRNA (147.4 ng), a 1 M HEPES buffer (12.5 μL), a 5 M aqueous sodium chloride solution (18.35 μL) and a 1 M aqueous GABA solution (62.5 μL) were mixed, diluted with UltraPure DNase/RNase-Free Distilled Water up to a liquid volume of 250 μL so as to obtain final concentrations: 8 ng/μL Cas9 protein, 0.68 ng/μL tracrRNA, 0.59 ng/μL MmDmd Ex51 crRNA, 50 mM HEPES, 250 mM GABA and 367 mM sodium chloride, and incubated at normal temperature for 15 minutes. Note that the addition amount of the 5 M aqueous sodium chloride solution was changed to 24.25 μL in the case of 485 mM sodium chloride and the addition amount was changed to 27.5 μL in the case of 550 mM sodium chloride, respectively.

Reaction Solution 3-2

Cas9 protein (2.0 μg), tracrRNA (170.9 ng), MmDmd Ex51 crRNA (147.4 ng), a 1 M HEPES buffer (12.5 μL), a 1 M aqueous potassium chloride solution (91.75 μL) and a 1 M aqueous GABA solution (62.5 μL) were mixed, diluted with UltraPure DNase/RNase-Free Distilled Water up to a liquid volume of 250 μL so as to obtain final concentrations: 8 ng/μL Cas9 protein, 0.68 ng/μL tracrRNA, 0.59 ng/μL MmDmd Ex51 crRNA, 50 mM HEPES, 250 mM GABA and 367 mM potassium chloride, and incubated at normal temperature for 15 minutes. Note that the addition amount of the 1 M aqueous potassium chloride solution was changed to 121.25 μL in the case of 485 mM potassium chloride and the amount was changed to 137.5 μL in the case of 550 mM potassium chloride.

Reaction Solution 3-3

Cas9 protein (2.0 μg), tracrRNA (170.9 ng), MmDmd Ex51 crRNA (147.4 ng), 1 M HEPES buffer (12.5 μL), a 1 M aqueous magnesium chloride solution (91.75 μL) and a 1 M aqueous GABA solution (62.5 μL) were mixed, diluted with UltraPure DNase/RNase-Free Distilled Water up to a liquid volume of 250 μL so as to obtain final concentrations: 8 ng/μL Cas9 protein, 0.68 ng/μL tracrRNA, 0.59 ng/μL MmDmd Ex51 crRNA, 50 mM HEPES, 250 mM GABA and 367 mM magnesium chloride, and incubated at normal temperature for 15 minutes. Note that the addition amount of the 1 M aqueous magnesium chloride was changed to 80.75 μL in the case of 323 mM magnesium chloride, and the amount was changed to 121.25 μL in the case of 485 mM magnesium chloride and to 137.5 μL in the case of 550 mM magnesium chloride, respectively.

Reaction Solution 3-4

Cas9 protein (2.0 μg), tracrRNA (170.9 ng), MmDmd Ex51 crRNA (147.4 ng), a 1 M HEPES buffer (12.5 μL), a 1 M aqueous magnesium aspartate solution 121.25 μL and a 1 M aqueous GABA solution (62.5 μL) were mixed, diluted with UltraPure DNase/RNase-Free Distilled Water up to a liquid volume of 250 μL so as to obtain final concentrations: 8 ng/μL Cas9 protein, 0.68 ng/μL tracrRNA, 0.59 ng/μL MmDmd Ex51 crRNA, 50 mM HEPES, 250 mM GABA and 485 mM magnesium aspartate, and incubated at normal temperature for 15 minutes. Note that the addition amount of the 1 M aqueous magnesium aspartate solution was changed at 137.5 μL in the case of 550 mM magnesium aspartate.

Reaction Solution 3-5

Cas9 protein (2.0 μg), tracrRNA (170.9 ng), MmDmd Ex51 crRNA (147.4 ng), a 1 M HEPES buffer (12.5 μL), a 5 M aqueous sodium chloride solution (19.8 μL), a 1 M aqueous magnesium chloride solution (11.3 μL), a 1 M aqueous potassium chloride solution (5.4 μL) and a 1 M aqueous GABA solution (62.5 μL) were mixed, diluted with UltraPure DNase/RNase-Free Distilled Water up to a liquid volume of 250 μL so as to obtain final concentrations: 8 ng/μL Cas9 protein, 0.68 ng/μL tracrRNA, 0.59 ng/μL MmDmd Ex51 crRNA, 50 mM HEPES, 250 mM GABA, 395.8 mM sodium chloride, 45.2 mM magnesium chloride and 21.4 mM potassium chloride, and incubated at normal temperature for 15 minutes.

Reaction Solution 3-6

Cas9 protein (2.0 μg), tracrRNA (170.9 ng), MmDmd Ex51 crRNA (147.4 ng), a 1 M HEPES buffer (12.5 μL), a 5 M aqueous sodium chloride solution (22.4 μL), a 1 M aqueous magnesium chloride solution (12.8 μL), a 1 M aqueous potassium chloride solution (6.1 μL) and a 1 M aqueous GABA solution (62.5 μL) were mixed, diluted with UltraPure DNase/RNase-Free Distilled Water up to a liquid volume of 250 μL so as to obtain final concentrations: 8 ng/μL Cas9 protein, 0.68 ng/μL tracrRNA, 0.59 ng/μL MmDmd Ex51 crRNA, 50 mM HEPES, 250 mM GABA, 447.4 mM sodium chloride, 51.1 mM magnesium chloride and 24.2 mM potassium chloride and incubated at normal temperature for 15 minutes.

Reaction Solution 4

Cas9 protein (800 ng), MmDmd Ex51 gRNA (200 ng), a 1 M HEPES buffer (0.05 μL) and a 5 M aqueous sodium chloride solution (5.5 μL) were mixed and diluted with UltraPure DNase/RNase-Free Distilled Water up to a liquid volume of 25 μL so as to obtain final concentrations: 16 ng/μL Cas9 protein, 4 ng/μL MmDmd Ex51 gRNA, 1 mM HEPES, 550 mM sodium chloride and 250 mM compound. To this solution, a predetermined amount of the compound stock solution was added so as to obtain a final concentration of 250 mM and the solution mixture was incubated at normal temperature for 15 minutes. Note that, in the cases where the final concentrations of the sodium chloride are 150 mM and 350 mM, a 5 M aqueous sodium chloride solution was added in amounts of 1.5 μL and 3.5 μL, respectively.

Reaction Solution 5

100 mg/mL FITC-Dextran (2.5 μL), a 1 M HEPES buffer (0.25 μL) and a 5 M aqueous sodium chloride solution (27.5 μL) were mixed and diluted with UltraPure DNase/RNase-Free Distilled Water up to a liquid volume of 250 μL so as to obtain final concentrations: 1 mg/mL fluorescein isothiocyanate-dextran (average mol wt 70,000) (FITC-Dextran), 1 mM HEPES, 550 mM sodium chloride and 250 mM compound. To this solution, a predetermined amount of a compound stock solution was added so as to obtain a final concentration to prepare a reaction solution.

Administration Solution 1

Cas9 protein (20 μg), mRosa26 gRNA (5 μg), 10×PBS (5 μL) and a 2.0 M aqueous 2'-deoxycytidine solution (6.25 μL) were mixed so as to obtain an aqueous solution having final concentrations of 400 ng/μL Cas9 protein, 100 ng/μL mRosa26 gRNA, 533 mM sodium chloride and 250 mM 2'-deoxycytidine. The concentration of the resultant solution was adjusted to be 533 mM with a 5 M aqueous sodium chloride solution, diluted with UltraPure DNase/RNase-Free Distilled Water up to a liquid volume of 50 μL and incubated at normal temperature for 15 minutes. Note that the addition amount of 5 M sodium chloride was appropriately controlled so as to satisfy a final concentration of each of 163 mM, 233 mM, 333 mM and 433 mM. The Cas9 protein herein was subjected to buffer replacement with 250 mM sodium chloride by use of Amicon® Ultra 2 mL Centrifugal Filters and then put in use.

Administration Solution 2

Cas9 protein (40 μg), mRosa26 gRNA (10 μg), 10×PBS (5 μL), and a 500 M compound stock solution (25 μL) were mixed so as to obtain final concentrations: 800 ng/μL Cas9 protein, 200 ng/μL mRosa26 gRNA, 533 mM sodium chloride and 250 mM compound. The concentration of the resultant solution was adjusted to be 533 mM with a 5 M aqueous sodium chloride solution, diluted with UltraPure DNase/RNase-Free Distilled Water up to a liquid volume of 50 μL and incubated at normal temperature for 15 minutes. Note that in the case of a compound having a final concentration of 25 mM, a 500 mM compound stock solution (2.5 μL) was added. The Cas9 protein herein was subjected to buffer replacement with 500 mM sodium chloride by use of Amicon® Ultra 2 mL Centrifugal Filters and then put in use.

Administration Solution 3

Cas9 protein (120 μg), hDMD Ex45 #1 gRNA (15 μg), hDMD Ex45 #23 gRNA (15 μg) and 10×PBS (25 μL) were mixed and a 500 mM compound stock solution was added, and then, 500 mM compound stock solution was added to the mixture so as to obtain final concentrations: 2400 ng/μL Cas9 protein, 300 ng/μL hDMD Ex45 #1 gRNA, 300 ng/μL hDMD Ex45 #23 gRNA, 158 mM sodium chloride, 25 mM or 250 mM compound and diluted with UltraPure DNase/RNase-Free Distilled Water up to a liquid volume of 250 μL and incubated at normal temperature for 15 minutes. The Cas9 protein herein was subjected to buffer replacement with 250 mM sodium chloride by use of Amicon® Ultra 2 mL Centrifugal Filters and then put in use

Method

Establishment of EGFP-SSA Reporter Cells

To evaluate uptake of Cas9 into a cell, an EGFP-SSA reporter cell line was established. C2C12 cells were transfected with a plasmid containing a reporter cassette of EF1α-EGxxFP-MmDMD-Ex51 (FIG. 1) in accordance with an electroporation method (NEPA21 transfection system). The electroporation using NEPA21 was carried out by using $1\times10^6$ cells under a poring pulse condition of 200 V and 5 ms. Thereafter, puromycin was added to a culture medium at a concentration of 1 mg/mL, and cells containing the reporter cassette of EF1α-EGxxFP-MmDMD-Ex51 were selected. Further in order to clone EGFP-negative cells, the cells were fractionated by a cell sorter (FACS Aria, BD) (FIG. 2).

Expression/Purification of Cas9 Protein

A protein-expressing plasmid having a desired gene was constructed with reference to pMJ806 described in the paper (Jinek, et al. 2012) as described later. More specifically, an expression vector was constructed by linking, to *S. pyogenes* Cas9 gene, 6×His tag sequence, an MBP sequence, a TEV protease cleavage sequence and two SV40 origin nuclear transfer (NLS) sequences (FIG. 3). *E. coli* strain BL21 (DE3) competent cell was transformed with the vector and allowed to overexpress the protein. The transformation was carried out in accordance with the protocol instructed by a manufacturer. The culture and purification were carried out with reference to the protocols described in the paper (Jinek, et al. 2012). Transformants were cultured while shaking in LB medium containing 0.1 mg/mL ampicillin sodium at 37° C. overnight. The culture solution was added to 2×YT culture and culture while shaking at 37° C. up to obtain an OD of 0.6. IPTG was added to the resultant medium, which was allowed to stand still on ice for 30 minutes and incubated while shaking at 16° C. for further 18 hours. The bacterial cells were centrifugally obtained and lysed with a lysis buffer. The lysate was centrifugally cleaned up and loaded on Ni-NTA Superflow Cartridges. In accordance with the protocol of the manufacturer of the Cartridges (Ni-NTA Superflow Cartridge Handbook), Cas9 protein with a His tag was eluted by use of imidazole gradient. To remove imidazole from the elution fractions, the fractions were subjected to gel filtration chromatography using HiLoad 26/60 Superdex (200 pg), and protein fractions were pooled. The protein fractions were subjected to TEV digestion according to a manufacturer's protocol, and then, to cleavage and separation of the 6×His-MBP tag and Cas9 protein. The protein solution after the TEV digestion was loaded in an Ni-NTA column. In accordance with a manufacturer's protocol, the 6×His-MBP tag was adsorbed and removed, and fractions containing Cas9 protein were collected from flow-through. The fractions collected were loaded in Resource S column, and Cas9 protein was allowed to elute by use of calcium chloride gradient. To remove calcium chloride in the elution buffer, gel filtration chromatography was carried out by HiLoad 26/60 Superdex 200 μg column equilibrated with GF buffer, with the result that a Cas9 protein fraction was recovered. The elution fraction was subjected to protein measurement carried out by Pierce 660-nm protein assay, SDS gel electrophoresis and Coomassie staining to determine the concentration and purity of the protein. After the purity was determined, filter sterilization was carried out.

The Papers Used as a Reference in Examples

Jinek, Martin, Krzysztof Chylinski, Ines Fonfara, Michael Hauer, Jennifer A Doudna, and Emmanuelle Charpentier, "A Programmable Dual-RNA-Guided DNA Endonuclease in Adaptive Bacterial Immunity", Science, 2012: 816-821

EGFP-SSA Assay

EGFP reporter cells were seeded in the corresponding medium at a density of $1\times10^4$/well in the wells of a 96 well plate and cultured at 37° C. for 24 hours in 5% $CO_2$. After the wells were washed with PBS 100 μL/well, reaction solution 1 or reaction solution 2 was added to the wells in a ratio of 50 μL/well and the cells were incubated at 37° C. for 30 minutes in 5% $CO_2$. Thereafter, the medium was replaced with C2C12 cell medium (100 μL/well) and culture was carried out at 37° C. for 48 hours in 5% $CO_2$. The medium was replaced with C2C12 cell medium containing HOECHST (registered trademark) 33342 in an amount of 1/2000 and culture was carried out at 37° C. for one hour in 5% $CO_2$. Thereafter, scanning was carried out by Opera Phenix (trademark) with EGFP/HOECHST/visible light. The images obtained were analyzed by Harmony (trademark) attached; the number of nuclei stained with HOECHST was counted; and the number of EGFP-positive cells was counted. The number of EGFP positive cells was counted based on whether EGFP was detected or not in the cell region stained with HOECHST. The EGFP positive rate per well was calculated in accordance with the following formula: EGFP positive rate (%)=(number of EGFP positive cells/number of nuclei stained with HOECHST)×100

Preparation of Human DMD Exon 45 Knock-in Mouse/Dmd Exon 44 Knock-Out Mouse

A knock-in vector (10 μg), which consists of a sequence (1.5 kb) including human DMD exon 45, a 5' side region (0.7 kb) and a 3' side region (0.6 kb), a neomycin resistance gene expression unit sandwiched by FRT sequences, and sequences derived from mouse Dmd intron 44 and intron 45 (each having 1.5 kb in size), was electroporated into $5\times10^3$ ES cells derived from a C57BL/6J mouse, together with a pCAG-Cas9 expression vector (2.5 μg) and two types of pU6-sgRNA expression vectors (target sequence; SEQ ID No. 7 and SEQ ID No. 8) (2.5 μg). A homologous recombination cell line was selected based on PCR and sequence confirmation. After the neomycin resistance unit was removed by a treatment with flippase (Flpe), the ES cell line was injected into a tetraploid blastocyst of ICR mouse under the microscope to obtain a chimeric mouse. The chimeric mouse and a female C57BL/6J mouse were subjected to in vitro fertilization to obtain a female human DMD exon 45 hetero knock-in mouse. Subsequently, to a fertilized egg between a male C57BL/6J mouse and a female human DMD exon 45 hetero knock-in mouse, a 100 ng/μL Cas9 mRNA (TriLink BioTechnologies), two types of sgRNAs (target sequence; SEQ ID No. 9 and SEQ ID No. 10, FASMAC) for knocking out mouse Dmd exon 44, and ssODN (50 ng/μL) (SEQ ID No. 11, Eurofins Genomics K.K.) were injected under the microscope. A gene of the male offspring thus obtained was subjected to genetic determination by PCR and sequence confirmation to select a human DMD exon 45 knock-in/mouse Dmd exon 44 knock-out mouse.

SEQ ID No. 7
5'-ATGAATGTGCCTACATATGG-3'

SEQ ID No. 8
5'-CATAGCATGCATTTGGCTTC-3'

SEQ ID No. 9
5'-GAATGAGGTAGTGTTGTAGG-3'

SEQ ID No. 10
5'-GCAGGAAATCATCTTATAGC-3'

SEQ ID No. 11
5'-GAGCAAGCTGGGTTAGAACAAAGGTCTGTCAGAGTCAGCATGGGAAT
GAGGTAGTGTTGTAGCAGGAAATAGTGTGGTTTAGGTCTCTCCCCGCCCT
CTGTGTATGTGTGTGTGTGTGTT-3'

Evaluation of DNA Mutation Introduction Efficiency Using mRosa26 gRNA in C57BL/6J Mouse To the right lower limb gastrocnemius of each of 9 weeks-old male C57BL/6J mice (CLEA Japan, Inc), administration solution 1 or administration solution 2 and PBS (50 μL) were administered. Administration solution 1 was administered to the same site once a day and 3 times in total. Administration solution 2 was administered only once. Four days after completion of the final administration, the mice were euthanized by cervical dislocation under anesthesia with 3.5% isoflurane, and the right lower limb gastrocnemius tissue was excised out and quickly frozen by dry ice. From the frozen muscle tissue, genomic DNA was extracted and purified by use of QIAamp Fast DNA Tissue Kit (Qiagen) and subjected to PCR using PrimeSTAR GXL DNA polymerase (TAKARA) (forward primer; SEQ ID No. 12; reverse primer; SEQ ID No. 13). The resultant PCR product was purified by QIAquick PCR purification kit (QIAGEN), treated with T7 Endonuclease I (NEB) and analyzed by Agilent 4200 TapeStation (Agilent). Based on the analysis value, mutation introduction efficiency was obtained in accordance with the following formula (Expression 1).

SEQ ID No. 12
5'-CTCCGAGGCGGATCACAAGCAATAATAACCTGTAG-3'

SEQ ID No. 13
5'-TGCAAGCACGTTTCCGACTTGAGTTGCCTCAAGAG-3'

$$f_{cut}=(b+c)/(a+b+c)$$

$$\text{indel }(\%)=100\times(1-\sqrt{(1-f_{cut})})$$ [Expression 1]

a: Area of peak derived from a band not cut out b, c: Areas of peaks derived from bands appearing at estimated molecular weights and cut out Evaluation of Exon Skipping Efficiency in Skeletal Muscle of Human DMD Exon 45 Knock-In/Mouse Dmd Exon 44 Knock-Out Mouse To the tibialis anterior muscle of each of 4 weeks-old male human DMD exon 45 knock-in/mouse Dmd exon 44 knock-out mice, administration solution 3 (50 μL) was administered once. Seven days after completion of the administration, a tibialis anterior muscle tissue was excised out and quickly frozen with dry ice. To the frozen muscle tissue, QIAzol Lysis Reagent (QIAGEN) was added. After the tissue was crushed and chloroform (WAKO) was added, the tissue was stirred/centrifuged, and then, a water phase containing RNA was separated and collected. Total RNA was subjected to reverse transcription using High Capacity RNA-to-cDNA kit (Thermo Fisher Scientific. Inc). Subsequently, a product with skipping was quantitatively measured by use of FastStart Universal Probe Master (Roche), the primers represented by SEQ ID Nos. 14 and 15 and the probe of sequence 16. The product without skipping was quantitatively measured by use of FastStart Universal Probe Master (Roche), the primers represented by SEQ ID Nos. 17 and 18 and the probe of sequence 19. Each of the PCR products was measured by use of ViiA7™ real time PCR system. In each amplification process, a standard product known in concentration was simultaneously amplified in order to calculate the absolute amount. For calculation, the software attached was used. Using the numerical value obtained by calculation, exon skipping efficiency was obtained in accordance with the following formula (Expression 2).

SEQ ID No. 14
5'-CGTGGCACAGATGGATTTCC-3'
(mEx43-46skipTaqF114: Thermo Fisher Scientific)

SEQ ID No. 15
5'-TTCTTTTGTTCTTCAATCCCTTGTC-3'
(mEx43-46skipTaqR191: Thermo Fisher Scientific)

SEQ ID No. 16
5'-ACTTCATAGAATGTACAAGGAA-3'
(FAM label, mEx43-46skipTaqP144: Thermo Fisher Scientific)

SEQ ID No. 17
5'-TCCTCAAAAACAGATGCCAGTATTC-3'
(hEx45 TaqF252: Thermo Fisher Scientific)

SEQ ID No. 18
5'-TCCTGCCACCGCAGATTC-3'
(hEx45 TaqR316: Thermo Fisher Scientific)

SEQ ID No. 19
5'-ACAGGAAAAATTGGGAAGC-3'
(FAM label, hEx45 TaqP278: Thermo Fisher Scientific)

$$\text{Exon skipping efficiency (\%)}=100\times a/(a+b) \quad \text{[Expression 2]}$$

a: Absolute amount of a product skipped b: Absolute amount of a product not skipped Evaluation of Intracellular Uptake Using Dextran C2C12 cells were seeded in wells of an 8-well chamber slide at a density of $1\times10^4$/well. On the following day, reaction solution 5 (250 μL) was added. Incubation was carried out at 37° C. for 30 minutes in 5% $CO_2$. After washing was made twice with a medium, incubation was made in the medium for 30 minutes or 90 minutes. Further, standing still was made with 4% paraformaldehyde/phosphate buffer solution at room temperature for 15 minutes. The fixed sample was embedded with ProLong™ Glass Antifade Mountant with NucBlue™ Stain and observed by a confocal laser scanning microscope.

Statistical Processing

As shown in FIG. 10 and FIG. 11, to find statistical significant difference between GABA and each conditions of the compounds, Dunnett's multiple comparison test using DNA mutation introduction efficiency, Indel (%), and exon skipping efficiency, was carried out. It was determined that if P value is less than 0.05, these is a statistically significant difference. Statistical processing was carried out by use of EXSUS Ver 8.0.

Example 1

Solutions for transductions containing each of compounds (A1) to (A5), and the (B) salt were prepared. To each of the solutions, a complex of gRNA and Cas9 protein was further dissolved. Mouse myoblasts (C2C12 cells) were contacted with each of the solutions in vitro, and target gene cleavage activity and cell viability were evaluated.

Evaluation of Activity of Compound for Transduction and Relative Comparison with GABA The activity of each of the compounds was evaluated by EGFP-SSA assay using a Cas9 protein/gRNA complex. EGFP reporter cells were seeded in the wells of a 96-well plate at a density of $1\times10^4$/well. On the following day, reaction solution 1 (50 μL) was added. Incubation was carried out at 37° C. for 30 minutes in 5% $CO_2$. The following operations were carried out in accordance with those of the EGFP-SSA assay. In a preparation, the compound stock solutions were diluted with UltraPure DNase/RNase-Free Distilled Water such that the final concentrations of the compounds fall within the range of 0.1 mM to 500 mM. The serial dilution samples of a compound were evaluated on the same plate. In each plate, three wells for 250 mM GABA and three wells for a solvent ($H_2O$) alone (not containing a compound) were prepared. Based on the number of HOECHST cells detected and the number of EGFP-positive cells per well, EGFP positive rates per concentration of individual compounds were calculated. The results are shown in FIG. 4.

Table 2 lists the EGFP positive rate and the number of HOECHST cells at the concentrations pointed by arrows in FIG. 4-1 and FIG. 4-2, and EGFP positive rate and the number of HOECHST cells of a positive control set on the same plate as the corresponding compound. The relative activities of each of the compounds were calculated in accordance with the following formulas (1) and (2) and shown in the graph of FIG. 5.

EGFP positive rate (relative ratio to GABA)=EGFP positive rate (%) at a predetermined concentration of compound/EGFP positive rate (%) of a positive control on the same plate (1)

Number of HOECHST-positive cells detected (relative ratio to GABA)=the number of HOECHST-positive cells detected at predetermined concentration of compound/the number of HOECHST cells detected in a positive control on the same plate (2)

TABLE 2

| Compound name | Compound activity/ cell number | | | GABA activity of each plate/cell number | | Relative ratio to GABA | |
|---|---|---|---|---|---|---|---|
| | Compound concentration (mM) | EGFP positive rate (%) | Number of HOECHST cells | EGFP positive rate (%) | Number of HOECHST cells | EGFP positive rate (%) | Number of HOECHST cells |
| 4-Hydroxyproline | 500.0 | 35.82% | 14088 | 0.91% | 22835 | 39.52 | 0.62 |
| N-Carbamyl-L-aspartic acid | 250.0 | 8.53% | 20622 | 1.09% | 17399 | 7.81 | 1.19 |
| 1-Methyl-L-histidine | 250.0 | 3.54% | 10899 | 0.70% | 16044 | 5.07 | 0.68 |
| 6-Phospho-D-gluconic acid | 250.0 | 2.61% | 19662 | 0.53% | 14966 | 4.94 | 1.31 |
| 1,3-Butylene glycol | 0.69 | 3.62% | 21720 | 1.04% | 21068 | 3.47 | 1.03 |
| 2-Hydroxyglutaric acid | 250.0 | 1.89% | 13367 | 0.70% | 16044 | 2.70 | 0.83 |
| 1,3-Dimethylurea | 500.0 | 2.64% | 14424 | 1.04% | 21068 | 2.53 | 0.68 |
| Creatinine | 200.0 | 2.27% | 19111 | 0.91% | 22835 | 2.50 | 0.84 |
| Miglitol | 125.0 | 1.55% | 18957 | 0.69% | 22950 | 2.25 | 0.83 |
| α-D-Glucose-1-phosphate | 250.0 | 2.52% | 21380 | 1.17% | 16563 | 2.15 | 1.29 |
| Disodium argininosuccinate hydrate | 200.0 | 1.97% | 9070 | 1.17% | 16563 | 1.68 | 0.55 |
| L-Carnosine | 125.0 | 1.76% | 22252 | 1.08% | 22690 | 1.63 | 0.98 |
| Cytidine | 125.0 | 2.24% | 16974 | 1.40% | 10738 | 1.60 | 1.58 |
| Sodium 3-methyl-2-oxobutate | 200.0 | 1.71% | 8789 | 1.17% | 16563 | 1.46 | 0.53 |
| Inosine 5'-disodium phosphate hydrate | 500.0 | 1.87% | 16922 | 1.34% | 10405 | 1.40 | 1.63 |
| Oxy-D-glucose-6-phosphate | 250.0 | 1.38% | 21521 | 1.17% | 20353 | 1.18 | 1.06 |
| 2'-Deoxyuridine | 100.0 | 1.10% | 18602 | 1.04% | 21068 | 1.06 | 0.88 |
| 2'-Deoxycytidine | 100.0 | 1.10% | 16691 | 1.17% | 16563 | 0.94 | 1.01 |
| GABA | 200.0 | 1.39% | 20111 | — | — | 1.00 | 1.00 |
| D(+)-cellobiose | 200.0 | 1.18% | 21440 | 1.46% | 21379 | 0.81 | 1.00 |
| Cytosine | 25.0 | 0.61% | 16470 | 1.46% | 21379 | 0.41 | 0.77 |
| Calcium pantothenate | 160.0 | 0.25% | 24792 | 1.17% | 16563 | 0.21 | 1.50 |

Example of a compound having a EGFP positive rate (transduction efficiency) that is 1.2 times or more higher than that of GABA include 4-hydroxyproline, N-carbamyl-L-aspartic acid, 1-methyl-L-histidine, 6-phospho-D-gluconic acid, 1,3-butylene glycol, 2-hydroxyglutaric acid, 1,3-dimethylurea, creatinine, miglitol, α-D-glucose-1-phosphate, disodium argininosuccinate hydrate, L-carnosine, cytidine, sodium 3-methyl-2-oxobutate and inosine 5'-disodium phosphate hydrate

[Example 2] Comparison of Activity of Compound for Transduction with iTOP-1250

The efficiency of introducing Cas9 protein/gRNA complex into a cell per compound was evaluated by the EGFP-SSA assay. EGFP reporter cells were seeded in the wells of a 96-well plate at a density of $1\times10^4$/well. On the following day, reaction solution 2 (50 μL) was added. Incubation was carried out at 37° C. for 30 minutes in 5% $CO_2$. In other wells, iTOP-1250 (50 μL) was added and incubation was carried out in the same manner. Subsequent operations were carried out in accordance with the EGFP-SSA assay. In a preparation, the compound stock solutions were diluted with UltraPure DNase/RNase-Free Distilled Water so as to obtain the final concentrations shown in Table 2. In each plate, wells containing 250 mM GABA and wells for a solvent ($H_2O$) alone (not containing a compound) were prepared. The relative ratio of the number of HOECHST cells detected and the EGFP positive cell rate to those of GABA per compound were calculated in accordance with the formulas (1) and (2) respectively. Calculation was carried out by using the data of three wells in a same plate and an average value thereof was plotted on a graph shown in FIG. 6, in which an error bar represents a standard deviation. Bar charts represented by the names of compounds show the results of cells when reaction solution 2 was used for treatment. Since the ratio of the EGFP positive rate of a positive control to that of a negative control was 2 or more, it was determined that the experiment was successfully carried out. "Untreated" in the graph represents a well containing no Cas9/gRNA and only washed with PBS. Example of a compound exhibiting an EGFP positive rate that was 1.2 times or more higher than iTOP-1250 include N-carbamyl-L-aspartic acid, sodium 3-methyl-2-sodium oxobutate, 2-hydroxyglutaric acid, disodium argininosuccinate hydrate, 2'-deoxycytidine, inosine 5'-disodium phosphate hydrate, 1-deoxynojirimycin, 2-deoxy-D-glucose-6-phosphate, L-carnosine, α-D-glucose-1-phosphate, creatinine, (R)-pantolactone, trimethadione and 6-phospho-D-gluconic acid.

Example 3

The efficiency of introducing Cas9 protein/gRNA complex into a cell in the case of the (B) salt was evaluated by the EGFP-SSA assay. EGFP reporter cells were seeded in the wells of a 96-well plate at a density of $1\times10^4$/well. On the following day, reaction solution 3-1, 3-2, 3-3, 3-4, 3-5 or 3-6 (50 μL) was added. Incubation was carried out at 37° C. for 30 minutes in 5% $CO_2$. In other wells, iTOP-1250 (50 μL) was added and incubation was carried out in the same manner. Subsequent operations were carried out in accordance with the EGFP-SSA assay. The number of HOECHST cells detected and EGFP positive cell rate obtained are shown in FIG. 7. The column of sodium chloride shows the cases where reaction solution 3-1 was used; the column of potassium chloride shows the cases where reaction solution 3-2 was used; the column of magnesium chloride shows the cases where reaction solution 3-3 was used; the column of magnesium aspartate shows the cases where reaction solution 3-4 was used; the column of "low concentration" of a mixed solution shows the cases where reaction solution 3-5 was used; the column of "high concentration" of a mixed solution shows the cases where reaction solution 3-6 was used; and the column of iTOP-1250 shows the cases where iTOP-1250 buffer was used. Calculation was carried out by using the data of three wells in a same plate and an average value thereof was plotted on a graph in which an error bar represents a standard deviation. The concentrations of ions ($Na^+$, $Mg^{2+}$, $K^+$, $Cl^-$) of inorganic salts serving as an electrolyte and contained in reaction solutions were expressed by milli equivalents (mEq/L). In all cases of salts, as the electrolytic ion concentration increases, EGFP positive rates increases. The case exhibiting the highest activity employed a mixture of three types of salts: sodium chloride, potassium chloride and magnesium chloride, and the activity of this case is high compared to the case of iTOP-1250. When sodium chloride and magnesium chloride were compared at the same electrolytic ion concentration, they exhibited almost the same activity.

[Example 4] Evaluation of the Efficiency of Introducing Cas9 Protein/gRNA Complex into a Cell at Each of the Concentrations of Sodium Chloride The efficiency of introducing Cas9/gRNA complex into a cell per compound at a different concentration of sodium chloride for (B) was evaluated by the EGFP-SSA assay. EGFP reporter cells were seeded in the wells of a 96-well plate at a density of $1\times10^4$/well. On the following day, reaction solution 3-7 (50 μL) was added. Incubation was carried out at 37° C. for 30 minutes in 5% $CO_2$. Subsequent operations were carried out in accordance with the EGFP-SSA assay. The compound (A) was added so as to have a final concentration of 250 mM. In each plate, wells containing 250 mM GABA and wells not containing a compound (i.e., $H_2O$ as a solvent alone) were prepared. Calculation was carried out by using the data of three wells in a same plate and an average value of EGFP positive cell rate was plotted on a graph shown in FIG. 8, in which an error bar represents a standard deviation. At a sodium chloride concentration of 150 mM to 550 mM, the EGFP positive rate of a well containing no compound was less than 1%. The EGFP positive rate of the well containing GABA at a sodium chloride concentration of 550 mM was 1.4% but the positive rate was less than 1% at a sodium chloride concentration of 150 mM and 350 mM. In contrast, the compounds exhibiting an EGFP positive rate of more than 1% at a sodium chloride concentration of 150 mM are N-carbamyl-L-aspartic acid and 6-phospho-D-gluconic acid. Particularly, 6-phospho-D-gluconic acid exhibited an EGFP positive rate of 2.2%, which was higher than that of GABA. Examples of a compound exhibiting a higher activity than a EGFP positive rate (1.4%) of GABA at a sodium chloride concentration of 350 mM were disodium argininosuccinate hydrate, N-carbamyl-L-aspartic acid, α-D-glucose-1-phosphate, 6-phospho-D-gluconic acid, 2-deoxy-D-glucose-6-phosphate and inosine 5'-disodium phosphate hydrate. The EGFP positive rates of compounds except 4-hydroxyproline at a sodium chloride concentration of 550 mM were all higher than that of GABA.

[Example 5] Evaluation of DNA-Mutation Introduction Efficiency at a Concentration of a Salt for (B) Using C57BC/6J Mouse A solution for transduction containing 2'-deoxycytidine as a compound (A3) and sodium chloride as the (B) salt was prepared. In the solution for transduction, a complex of mRosa26 gRNA and Cas9 protein was further dissolved. The resultant solution was used as an administration solution of Example 5 (administration solution 1, see "preparation" above). Administration solution 1 was locally administered to the mouse right lower limb gastrocnemius and the activity to cleave a target gene was evaluated. Administration solution 1 was prepared so as to have a sodium chloride concentration of 163 mM, 233 mM, 333 mM, 433 mM or 533 mM. Administration solution 1 was administered at a dose of 50 μL per time for 3 consecutive days. Four days after completion of final administration, the right lower limb gastrocnemius tissue was excised out and subjected to T7E1 assay. The results of the assay are shown in FIG. 9. Genome editing was confirmed in normal mice at any salt concentration.

[Example 6] Evaluation of DNA-Mutation Introduction Efficiency at Different Concentration of a Compound (A) Using C57BC/6J Mouse A solution for transduction containing any one of compounds (A1) to (A5) and sodium chloride as the (B) salt was prepared. In the solution for transduction, a complex of mRosa26 gRNA and Cas9 protein was further dissolved. The resultant solution was used as an administration solution of Example 6 (administration solution 2, see "preparation" above). Administration solution 2 was locally administered to the mouse right lower limb gastrocnemius and the activity to cleave a target gene was evaluated. Administration solution 2 was prepared by adding 2'-deoxycytidine, 6-phospho-D-gluconic acid, N-carbamyl-L-aspartic acid or 2-deoxy-D-glucose-6-phosphate as the compound so as to have a final concentration in the administration solution of 25 mM or 250 mM. Administration solution 2 was administered once at a dose of 50 μL. Four days after completion of administration, the right lower limb gastrocnemius tissue was excised out and subjected to T7E1 assay. The results of the assay are shown in FIG. 10. Any one of the compounds exhibited a genome editing efficiency that is equivalent or higher to that of 250 mM GABA as a control compound in normal mice. In particular, N-carbamyl-L-aspartic acid and 2-deoxy-D-glucose-6-phosphate exhibited statistically significant results compared to GABA.

[Example 7] Exon Skipping Effect in the Cases where h DMD Ex45 #1 gRNA and hDMD Ex45 #23 gRNA were Used in Human DMD Exon Knock-in/Mouse Dmd Exon 44 Knock-Out Mice A solution for transduction containing any one of compounds (A1) and (A4) and sodium chloride as the (B) salt was prepared. In the solution for transduction, a complex of hEx45 #1 gRNA, hEx45 #23 gRNA and Cas9 protein was further dissolved. The resultant solution was used as an administration solution of Example 7 (administration solution 3, see, "preparation" above). Administration solution 3 was locally administered to the tibialis anterior muscle, and the skipping efficiency of human DMD exon 45 sequence was evaluated. Administration solution 3 was prepared by adding 6-phospho-D-gluconic acid or N-carbamyl-L-aspartic acid as the compound or GABA as a control so as to have a final concentration in the solution of 25 mM or 250 mM. Administration solution 3 was administered once at a dose of 50 μL. On the 7th day, the tibialis anterior muscle tissue was excised out and subjected to determination of exon skipping efficiency. The results of the assay are shown in FIG. 11. Any one of the compounds exhibits high exon skipping activity in a target gene (dystrophin gene) than 250 mM-GABA in hEx45KI-mdx44 mice. In particular, 25 mM N-carbamyl-L-aspartic acid exhibited statistically significant results compared to 250 mM GABA.

[Example 8] Intracellular Uptake Test Using Dextran

Intracellular uptake was evaluated in C2C12 cells by use of a fluorescent-labeled dextran (FITC-dextran). The concentration of sodium chloride was 550 mM. The final concentration of the compounds are 250 mM for GABA (control), 125 mM for N-carbamyl-L-aspartic acid and 250 mM for 2-deoxy-D-glucose-6-phosphate (numerals represent final concentrations). Reaction solution 5 containing each of the compounds was added to the cells. Thirty minutes later, the cells were placed in a culture medium and incubated for 30 minutes or 90 minutes. The results are shown in FIG. 12. It was found that the compounds defined by the present invention is used in combination with a salt, intracellular permeation of the fluorescent labeled dextran is promoted. It was confirmed that not only protein (Cas9) and nucleic acid (gRNA) but also a high molecular compound such as dextran can be highly efficiently delivered by the present invention.

INDUSTRIAL APPLICABILITY

The solution for transduction of the present invention and the transduction method of the present invention using the solution enable to highly efficiently deliver a molecule(s) of interest such as a nucleic acid and a protein into various types of cells. For example, when a complex of gRNA and Cas protein used in the CRISPR system is contacted with cells together with the solution for transduction of the present invention, the complex can be highly efficiently introduced into the cells to attain genome editing by the CRISPR system. The transduction method of the present invention makes it possible to efficiently produce cells having a molecule(s) of interest such as a nucleic acid and protein transduced therein.

The invention claimed is:

1. A pharmaceutical composition comprising:

a solution for transduction comprising:

at least one compound selected from the group consisting of 1-methyl-L-histidine, N-carbamyl-L-aspartic acid, 2-deoxy-D-glucose-6-phosphate, 6-phospho-D-gluconic acid, and a salt thereof, (B) a salt, and a Cas protein and/or gRNA.

2. A method for transducing a molecule(s) of interest into a cell, comprising a step of contacting the cell with the molecule(s) of interest and a solution for transduction, wherein the solution for transduction comprises: at least one compound selected from the group consisting of 1-methyl-L-histidine, N-carbamyl-L-aspartic acid, 2-deoxy-D-glucose-6-phosphate, 6-phospho-D-gluconic acid, and a salt thereof; and (B) a salt, and wherein the molecule(s) of interest is a Cas protein and/or gRNA.

3. The method according to claim 2, wherein the (B) salt is at least one selected from the group consisting of sodium chloride, magnesium chloride and potassium chloride.

4. The method according to claim 2, wherein the cell is present in a living body.

5. The method according to claim 2, wherein the cell is a muscle cell.

6. A method for producing a cell having a molecule(s) of interest transduced therein, comprising a step of contacting the cell with a molecule(s) of interest and a solution for transduction, wherein the solution for transduction comprises: at least one compound selected from the group consisting of 1-methyl-L-histidine, N-carbamyl-L-aspartic acid, 2-deoxy-D-glucose-6-phosphate, 6-phospho-D-gluconic acid, and a salt thereof; and (B) a salt, and wherein the molecule(s) of interest is a Cas protein and/or gRNA.

7. The method according to claim 6, wherein the (B) salt is at least one selected from the group consisting of sodium chloride, magnesium chloride and potassium chloride.

8. The method according to claim 6, wherein the cell is present in a living body.

9. The method according to claim 6, wherein the cell is a muscle cell.

* * * * *